US009820799B2

(12) United States Patent
Schwagten et al.

(10) Patent No.: US 9,820,799 B2
(45) Date of Patent: *Nov. 21, 2017

(54) IMPLANT DEVICE AND SYSTEM FOR ABLATION OF A RENAL ARTERIAL WALL FROM THE INSIDE

(71) Applicant: MEDICAL DEVELOPMENT TECHNOLOGIES S.A., Fentange (LU)

(72) Inventors: Bruno Schwagten, Lint (BE); Glenn Van Langenhove, Merelbeke (BE)

(*) Notice: Subject to any disclaimer, the term of this patent is extended or adjusted under 35 U.S.C. 154(b) by 342 days.

This patent is subject to a terminal disclaimer.

(21) Appl. No.: 14/390,263

(22) PCT Filed: Oct. 1, 2012

(86) PCT No.: PCT/EP2012/069382
§ 371 (c)(1),
(2) Date: Oct. 2, 2014

(87) PCT Pub. No.: WO2013/149684
PCT Pub. Date: Oct. 10, 2013

(65) Prior Publication Data
US 2015/0157385 A1    Jun. 11, 2015

(30) Foreign Application Priority Data
Apr. 2, 2012 (WO) ................ PCT/EP2012/055999

(51) Int. Cl.
A61B 18/10    (2006.01)
A61B 18/08    (2006.01)
A61B 18/00    (2006.01)

(52) U.S. Cl.
CPC ............ *A61B 18/10* (2013.01); *A61B 18/082* (2013.01); *A61B 2018/0072* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01);
(Continued)

(58) Field of Classification Search
CPC .................. A61B 18/10; A61B 18/082; A61B 2018/00708; A61B 2018/00577; A61B 2018/00214; A61B 2018/00714; A61B 2018/00434; A61B 2018/00404; A61B 2018/00791; A61B 2018/00678; A61B 2018/0072; A61B 2018/00511
See application file for complete search history.

(56) References Cited

U.S. PATENT DOCUMENTS 6,632,223 B1   10/2003 Keane
6,802,857 B1   10/2004 Walsh et al.
(Continued)

FOREIGN PATENT DOCUMENTS

EP    1036574 A1    9/2000

Primary Examiner — Jaymi Della
Assistant Examiner — Eunhwa Kim
(74) Attorney, Agent, or Firm — Clark & Elbing LLP; Susan M. Michaud

(57) ABSTRACT

The current invention concerns systems, devices and methods for the ablation of a vessel's wall from the inside, more specifically to implant devices and to the ablation of the wall of one or more renal arteries from the inside, preferably transmural ablation. Hereby, one or more implant devices can be implanted in the vessels and can subsequently be heated by external energy-providing means.

17 Claims, 27 Drawing Sheets

(52) U.S. Cl.
CPC ............... *A61B 2018/00678* (2013.01); *A61B 2018/00708* (2013.01); *A61B 2018/00714* (2013.01); *A61B 2018/00791* (2013.01)

(56) References Cited

U.S. PATENT DOCUMENTS

| | | | |
|---|---|---|---|
| 7,235,096 | B1 | 6/2007 | Van Tassel et al. |
| 8,073,551 | B2 | 12/2011 | McCann et al. |
| 2002/0002399 | A1* | 1/2002 | Huxel ................... A61F 2/88 623/1.15 |
| 2002/0183829 | A1 | 12/2002 | Doscher et al. |
| 2003/0139739 | A1 | 7/2003 | Doscher et al. |
| 2003/0187445 | A1 | 10/2003 | Keith et al. |
| 2004/0116965 | A1 | 6/2004 | Falkenberg |
| 2004/0215310 | A1* | 10/2004 | Amirana ............. A61B 18/14 623/1.11 |
| 2005/0021088 | A1 | 1/2005 | Schuler et al. |
| 2005/0027306 | A1 | 2/2005 | Krivoruchko et al. |
| 2005/0101946 | A1* | 5/2005 | Govari ................ A61B 18/14 606/33 |
| 2006/0095103 | A1 | 5/2006 | Eggers et al. |
| 2006/0116666 | A1 | 6/2006 | Cornelius et al. |
| 2008/0319247 | A1 | 12/2008 | Forbes et al. |
| 2009/0210050 | A1 | 8/2009 | Van Tassel et al. |
| 2010/0225174 | A1* | 9/2010 | Jiang .................. A61N 1/3787 307/104 |
| 2011/0288543 | A1* | 11/2011 | Cheng ............... A61B 18/1233 606/41 |
| 2011/0307034 | A1* | 12/2011 | Hastings ........... A61B 18/1206 607/61 |
| 2015/0150621 | A1 | 6/2015 | Schwagten et al. |

* cited by examiner

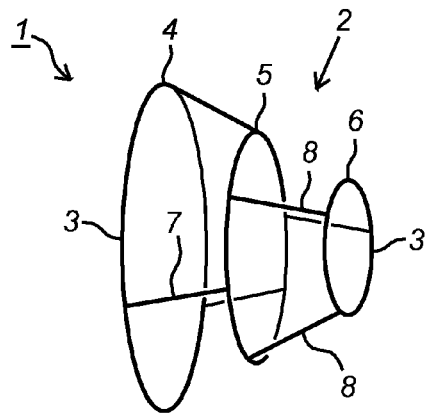
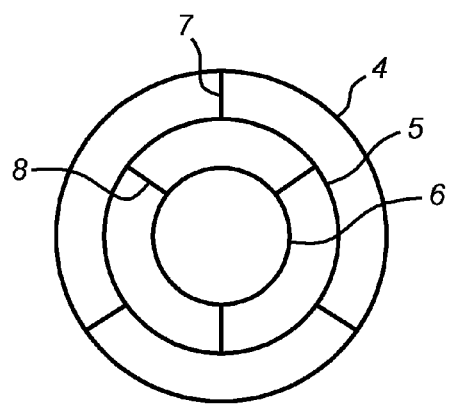
Fig. 1a                Fig. 1b
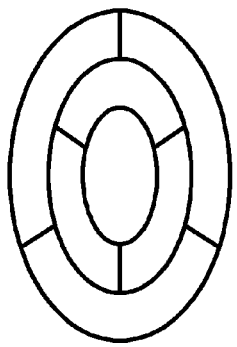
Fig. 1c
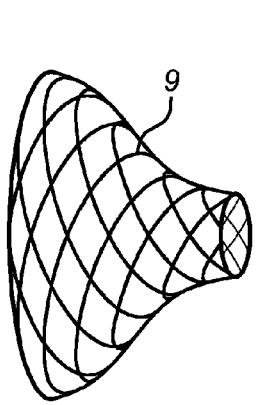
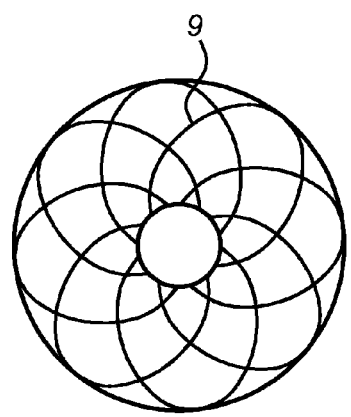
Fig. 2a                Fig. 2b

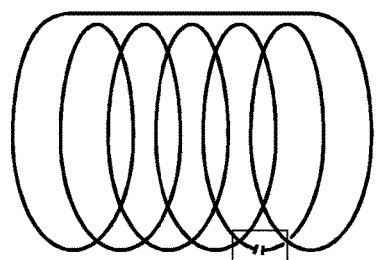
*Fig. 19*
*Fig. 19a*
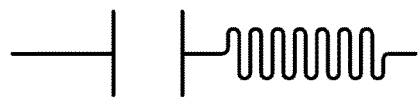
*Fig. 19a*
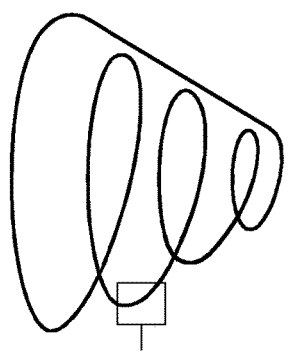
*Fig. 20*
*Fig. 20a/b*
*Fig. 20a*
*Fig. 20b*

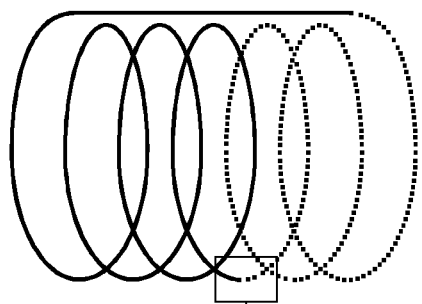
Fig. 21
Fig. 21a
Fig. 21a
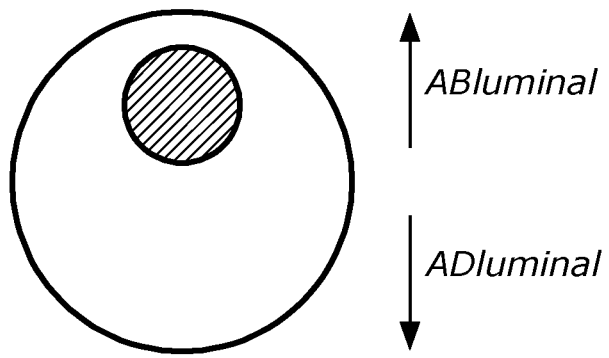
Fig. 22

IMPLANT DEVICE AND SYSTEM FOR ABLATION OF A RENAL ARTERIAL WALL FROM THE INSIDE

CROSS-REFERENCE TO RELATED APPLICATIONS

This application is the U.S. National Phase under 35 U.S.C. §371 of International Application PCT/EP2012/069382, filed Oct. 1, 2012, which claims priority to PCT/EP2012/055999, filed Apr. 2, 2012.

TECHNICAL FIELD

The invention pertains to the technical field of the treatment of bodily vessels by means of ablation, more specifically to the treatment of conditions such as arterial hypertension. In particular, the present invention relates to systems, devices and methods for the ablation of a vessel's wall from the inside, more specifically to implant devices and to the ablation of the wall of one or more renal arteries from the inside, preferably transmural ablation.

BACKGROUND

The present invention concerns a system of one or more implant devices and excitation device, an implant device and a method using the system and one or more devices for the treatment of arterial and venous structures.

The present invention also concerns implant devices, a system of implant devices and external excitation means, and a method for positioning one or more implant devices in a vessel, and subsequently heating these implant devices, preferably simultaneously, thereby transferring heat from implant devices to the vessel's inner wall.

The general concept of the present invention is to implant one or more implant devices into vessels, said implant devices making contact with the vessels' inner walls at the positions where ablation is deemed necessary. In contrast with prior art, ablation is not performed immediately, but the one or more implant devices can be heated up to a specified temperature by external energy-providing means, which are spatially separated from, i.e. not touching, the implant device and able to provide energy remotely to the implant device for increasing the temperature of the ablation region of the implant device up to an ablation temperature. In a preferred embodiment, an implant device comprises an area which is made from a material which may show magnetic hysteresis and the external energy-providing means are able to create a time-varying magnetic field at the position of the implanted device, hereby heating the implant through the phenomenon of magnetic hysteresis. The maximum temperature the implant device can reach, is limited by the Curie or Néel temperature of the magnetic material used, above which temperature the magnetic hysteresis effect disappears. This Curie or Néel temperature can be engineered precisely to the necessary ablation temperature e.g. by changing the composition of the magnetic alloy that is used. In another embodiment, non-magnetic material may be used, and insulation material may then be used to provide sufficient temperature-controlling means. In an embodiment, the heating of the implant device is done by Joule heating or direct heating, or any other heating system.

The implant device according to the present invention can thus be used in arterial and venous structures.

Indeed, the system, device and method according to the present invention can also be used to perform ablation throughout the renal arteries, to perform ablation of the nervous system surrounding the renal arteries, to perform ablation of the renal sympathetic nerves, more specific to perform ablation of the renal sympathetic nerves in the adventitia surrounding the renal arteries, to perform ablation of renal afferent and/or efferent nerves.

The device can be used in the renal arteries in which case the device, system and method can be used to treat arterial hypertension, norepinephrine spillover, heart failure, hypertension related target organ damage, etc.

The device can be used in the renal arteries in which case the device, system and method can be used to treat arterial hypertension, more specific, but not limited to, mild, moderate and/or severe hypertension, masked hypertension, white-coat hypertension, reverse dipping hypertension, non-dipping hypertension, dipping hypertension end neuroadrenergic hypertension.

The devices, systems and methods as described in this document may also be used in human or animal corpses or in models of human or animal bodies, e.g. for practicing or educational purposes, whereby the heating of the implant devices leaves ablation marks on the vessel's inner wall which can be used to check if the implant devices were positioned correctly and sufficient ablation occurred.

The present document focuses its description on the application of the device inside the renal arteries.

A person skilled in the art will be able to interpret the device, the system and the method and to provide them of specific features, components or steps if to be used in other areas.

Human wellbeing is menaced by numerous disorders which change with time. The art of medicine continuously needs to innovate and to adapt to these changes.

US patent application 2005/0027306 discloses a catheterization device for delivering a self-expanding stent. The device has an inner shaft and an outer shaft moveable with respect to the inner shaft. The self-expanding stent is received on the inner shaft adjacent its distal end. A tapered tip is located on the inner shaft distal end and it forms a smooth transition from the delivery device to a guidewire extending therethrough. A handle allows a practitioner to deploy the stent single handedly. The stent may have its segments in a first radial configuration for delivery of the stent or the stent may have a plurality of segments in a first radial configuration and a plurality of second segments in a second radial position.

US patent application 2005/0101946 discloses a method and system for treating AF by ablation of a pulmonary vein, using a stent which has a resonant circuit. The stent can be implanted at the site of ablation and subsequently activated by external energy-providing means, in particular by an electromagnetic field with the resonating frequency of the resonant circuit of the stent. The application does not disclose the possibility of using materials which show magnetic hysteresis for at least part of the stent, and to use the hysteresis effect for activating the stent. Thereby, it is also in this way not easy to control the ablation temperature of the stent. The energy delivered to the stent should be monitored very closely as it depends on a multitude of factors and the temperature of the stent is not under control, such as the electrical resistance of the stent and the resonant circuit of the stent, the magnitude of the RF field at the site of the stent, the quality of the thermal contact between stent and vessel wall.

European patent application EP 1 036 574 discloses a device and method for heating an implanted stent up to a certain temperature, using external energy-providing means.

The stent can be heated up through the effect of magnetic hysteresis. However, in this patent application, the temperature is controlled by an external controlling system which measures the temperature of the stent via e.g. an infrared camera, and alters the energy provided with the external energy-providing means accordingly. Hereby, it is not explicitly disclosed that the system is used for ablation. Furthermore, the temperature is controlled by an external feedback system, and not e.g. by the material properties of the stent. Moreover, European patent application EP 1 036 574 does not disclose that the stent or implant may subtend at least a substantially complete circumferential band of the vessel's inner wall.

U.S. Pat. No. 7,235,096 discloses an implantable stent for treating a damaged body lumen, which comprises tubular stent body having several interconnected microholes distributed throughout the body uniformly along the entire length of the body. The tubular stent body has several interconnected microholes distributed throughout the stent body substantially uniformly along the entire length of the stent body; the several microholes are small so as to promote an organized growth pattern of infiltrating cells throughout the stent body, and the stent body is otherwise substantially free of holes larger than the microholes; the stent body is formed from a fibrous three dimensional non-woven matrix. The patent also discloses a stent system comprising the stent in spaced juxtaposition to an energy source for transcutaneously applying energy to the stent, thereby causing the temperature of the stent to increase to a temperature above body temperature (preferably 38-49° C.). It further discloses an active stent comprising the stent and further comprising live cells growing in the interconnected microholes. A method for measuring flow of a fluid through a body lumen is disclosed, involving: implanting the stent into a body lumen having a flow of fluid through it; energizing the implanted stent transcutaneously to raise its temperature above body temperature; monitoring transcutaneously the output from at least one of the temperature sensors upon cessation of the energizing to determine the cooling rate at each of the at least one sensor: and obtaining the flow rate of the fluid through the stent from the cooling rate at the at least one sensor. Also disclosed is a method for treating a tubular body organ in a subject involving: promoting the ingrowth of living cells in the stent; and implanting the stent into the tubular organ of the subject prior to or following promoting the ingrowth of the living cells so as to treat the tubular organ, whereby the stent body is formed from a fibrous three dimensional non-woven matrix.

In U.S. Pat. No. 7,235,096, the temperature of the stent can be controlled by an at least partially external control system. In this case, the temperature sensor or sensors transmit the measured temperature to said external control system, which then controls the external energy source. Further, in this patent, the temperature of the stent can be controlled by the use of material with a Curie temperature whereby the heating of the stent occurs via hysteresis heating. Hereby the temperature of the stent is limited to the Curie temperature, since the mechanism of hysteresis heating only works below the Curie temperature. Both temperature control mechanisms, i.e. the external control system and the use of magnetic materials, have their shortcomings.

The mechanism comprising the external control system leads to the necessity of a dedicated external energy source, specifically adapted for receiving the temperature from the temperature sensor. Furthermore, in such a system the energy source, which in most cases will be a radiofrequent field, will need to be controlled in intensity and possibly also in frequency in order for the implant to be kept at a desired temperature.

The mechanism of hysteresis heating has a number of difficulties, especially in finding the correct alloy with an optimal Curie temperature. As this optimal temperature may be different case-by-case, a different alloy may need to be found for different temperatures.

There remains a need in the art for improved devices, systems and methods for the ablation of a substantially complete circumferential band or a spiraling band around a vessel's wall from the inside. The present invention aims to resolve at least some of the problems mentioned above, e.g. to make sure that the ablation is performed for a substantially complete circumferential band or a spiraling band around a vessel's wall from the inside, that the ablation itself can be triggered with external means and this multiple times if necessary, that the ablation temperature is well under control and does not depend on less-controlled elements in the treatment or on an intricate monitoring system, etc.

The present invention tries to overcome the problems by providing an implant with a built-in temperature control and/or measuring means, whereby said control means are capable of keeping the temperature of at least part of the implant to or below a desired temperature. The present invention also provides a system and method for heating an implant to or up to a desired maximal temperature.

SUMMARY OF THE INVENTION

The present invention provides a system of one or more implant devices and excitation device, an implant device and a method using the system and one or more devices for the treatment of arterial and venous structures. The present invention also concerns implant devices, a system of implant devices and external excitation means, and a method for positioning one or more implant devices in a vessel, and subsequently heating these implant devices, preferably simultaneously, thereby transferring heat from implant devices to the vessel's inner wall.

In a first aspect, the present invention provides a system for ablation of at least a part of a vessel's wall from the inside, comprised of
  a self-expanding implant device, adapted to be implanted and deployed within said vessel; whereby said implant comprises an ablation region along at least a portion of its length, said ablation region being adapted for surface contact with said vessel and said ablation region subtending at least a substantially complete circumferential band or a spiraling band and being effective to ablate a signal-blocking path within said vessel upon application of energy to the implant;
  external energy-providing means, which are spatially separated from the implant device and able to provide energy to the implant device for increasing the temperature of the ablation region of the implant device up to an ablation temperature.

In a preferred embodiment, the system comprises more than one implant device, each of which adapted to be implanted and deployed within one or more vessels. These implant devices can each be adapted to be implanted and deployed within one or more renal arteries.

In a particular preferred embodiment, one or more implant devices of the system comprise a proximal portion having a first diameter and a distal portion having a second diameter that is less than the first diameter and that is sufficient to enable said implants to seat within one or more vessels.

In a preferred embodiment, at least part of the one or more implant devices of the system is made from at least one material which shows magnetic hysteresis, such as a ferromagnetic, ferrimagnetic or anti-ferromagnetic material. Furthermore, the external energy-providing means may create a time-varying magnetic field at the position of the one or more implant devices. In a more preferred embodiment, this time-varying magnetic field is created by an electric coil through which a time-varying electrical current is sent.

In another embodiment, the system also comprises
a sheath suitable for transporting and delivering the one or more implant devices to or near the desired position in the one or more vessels;
a guidewire suitable for sequentially guiding the sheath with the one or more implants to the desired position in the one or more vessels.

In a second aspect, the present invention provides a self-expanding implant device adapted to be implanted and deployed within a vessel; said implant comprising an ablation region along at least a portion of its length, the ablation region being adapted for surface contact with the vessel and the ablation region subtending at least a substantially complete circumferential band or a spiraling band and being effective to ablate a signal-blocking path within the vessel upon application of energy to the implant; whereby said ablation region comprises at least one material which shows magnetic hysteresis, such as a ferromagnetic, ferrimagnetic or anti-ferromagnetic material.

In a similar aspect, the present invention provides a, preferably self-expanding, implant device adapted to be implanted and deployed within a vessel, said implant comprising an ablation region along at least a portion of its length, the ablation region being adapted for surface contact with the vessel and for subtending at least a substantially complete circumferential band or a spiraling band and said ablation region effective to ablate a signal-blocking path within the vessel upon application of energy to the implant device, whereby preferably said ablation region comprises at least one material which shows magnetic hysteresis, such as a ferromagnetic, ferrimagnetic or anti-ferromagnetic material.

In another similar aspect, the present invention provides an implant comprising an electrical circuit comprising a pick-up coil, a heater coil and a temperature-controlled switch which comprises a closed position and an interrupted position. Said switch preferably comprises a bi-metallic component and/or a thermistor, such as a PTC thermistor and/or said switch preferably comprises a temperature sensor and a, preferably digital, thermostat connected to said sensor and to said switch for interrupting said switch and thus said electrical circuit when said sensor measures a pre-determined temperature.

In a preferred embodiment, the implant device comprises a shape which is adapted for a renal artery. In a more preferred embodiment, said ablation region of said implant device is adapted for surface contact with said renal arteries and for subtending at least a substantially spiraling band, e.g. for treating arterial hypertension by ablation and consequential blocking renal sympathetic nerve signals.

In a particular preferred embodiment, parts of the implant device are made from more than one material showing magnetic hysteresis and which have different Curie or Néel temperatures.

In a more preferred embodiment the implant device is suitable for long-term implantation. In another preferred embodiment, the implant device is a bio-resorbable implant device or an implant that disappears, e.g. by evaporation, after one or more ablations. Furthermore, the implant device may comprise a proximal portion having a first diameter and a distal portion having a second diameter that is less than the first diameter and that is sufficient to enable said implant device to seat within a vessel. The implant device may further comprise anchoring means at or near the proximal or distal portion of said implant device, said anchoring means being suitable for keeping the device at or near the same position compared to the vessel's inner wall.

In a preferred embodiment, part of said implant device which can come into contact with the patient's blood when said implant device is implanted, is thermally isolated from the rest of the implant device such that the blood is not heated or overheated during the excitation of the implant device. Such part can comprise an adluminal coating or a layer with high isolation characteristics.

In a preferred embodiment, said implant comprises a thermoactive coating comprising an activation temperature between 35° C. and 37° C. so that the body temperature would trigger activation. In an alternatively preferred embodiment, said implant comprises a thermoactive coating comprising an activation temperature above 45° C. so that activation is triggered only when said ablation region is heated by said external energy-providing means.

In a preferred embodiment, the implant device comprises a core region of material with a certain Curie temperature, surrounded by other material with thermal and/or elastic properties suitable for the implant device's purpose.

In an embodiment, said implant comprises substances capable of producing a lesion of limited necrosis and/or neurotoxicity.

In a preferred embodiment, the implant device comprises cavities which are filled with one or more substances and which open when the implant is heated. In a more preferred embodiment, these substances are mixed before being released into the patient's body or vessel wall, e.g. to deliver a two-component neurotixine. In another preferred embodiment, these substances are a selection or a composition of one or more of the following substances:
ethanol;
tetrodotoxin and batrachotoxin;
maurotoxin, agitoxin, charybdotoxin, margatoxin, slotoxin, scyllatoxin or hefutoxin;
calciseptine, taicatoxin, calcicludine, or PhTx3;
botulinum toxide;
cytochalasin D, rapamycin, sirolimus, zotarolimus, everolimus, paclitaxel;
glutamate;
isoquinoline;
N-methyl-(R)-salsolinol;
Beta-carboline derivates.

In a further aspect, the present invention provides a system comprising one, two, three, four or more implant devices, such as 5, 6, 7, 8, 9 or 10 or more implant devices according to the present invention. Preferably this system comprises external energy-providing means, which are spatially separated from said implant devices and able to provide energy to said implant devices for increasing the temperature of the ablation regions of the implant devices up to an ablation temperature, and/or a sheath suitable for transporting and delivering the one or more implant devices to or near the desired position in the one or more vessels, and/or a guidewire suitable for sequentially guiding the sheath with the one or more implants to the desired position in the one or more vessels. In a preferred embodiment, the system comprises one or two implant devices according to the present invention, each of which adapted for a corresponding renal artery.

In yet a further aspect, the present invention provides a method for the treatment of a patient with arterial hypertension by blocking renal sympathetic nerve signals via ablation of a substantially complete circumferential band or a spiraling band on one or more renal arteries' walls from the inside, comprising the steps of implanting one or more implant devices in one or more renal arteries by means of a sheath and a guidewire, said implant devices each comprising an ablation region along at least a portion of their length, said ablation regions being adapted for surface contact with said renal arteries and said ablation regions subtending at least a substantially complete circumferential band or a spiraling band and being effective to ablate a signal-blocking path within said renal arteries upon application of energy to said implant devices;

retracting the sheath and guidewire;

subsequently heating the ablation region of the one or more implant devices by external energy-providing means, which are spatially separated from the implant device.

In a similar aspect, the present invention provides a method for heating one, two or more implant devices, which are suitable to be implanted in one, two or more vessels, comprising the steps of:

subsequently positioning said implant devices in said vessels by means of a sheath and a guidewire, said implant devices each comprising an ablation region along at least a portion of their length, said ablation region subtending at least a substantially complete circumferential band or a substantially spiraling band, said implant devices effective for ablating a signal-blocking path within said vessels upon application of energy to said implant devices;

retracting the sheath and guidewire;

heating the ablation region of said implant devices by external energy-providing means which are spatially separated from said implant devices characterized in that said heating occurs after said sheath and guidewire are retracted and said heating of said implant devices occurs simultaneously.

In a preferred embodiment of the method, a recovery period is observed prior to heating the ablation region of the one or more implant devices by external energy-providing means. Furthermore, this recovery period may be long enough to allow the one or more implant devices to be integrated into the vessel wall or endothelialized.

In a particular preferred embodiment of the method, the step of heating the ablation region of the one or more implant devices by external energy-providing means, which are spatially separated from the implant device, is performed more than once, e.g. at well-spaced time-intervals, whenever it is deemed necessary, etc.

In a more preferred embodiment of the method, one or more implant devices as described in this document are being used.

In a still more preferred embodiment of the method, use is made of a system as described in this document.

DESCRIPTION OF FIGURES

FIGS. 1 to 5, and 9 to 11 schematically represent different embodiments of an implant for the treatment of arterial and venous structures according to the invention.

FIG. 19 shows an embodiment of an implant comprising a fuse, so that at certain temperatures, the circuit that may be generated gets interrupted. FIG. 19a shows a detailed view of the fuse.

In a different configuration, as shown in FIG. 20, the metal implant can be build up of memory shape alloys. Details of the on and off position of the switch or fuse are shown in FIGS. 20a and 20b respectively.

In a still different configuration as shown in FIG. 21 and a detail in FIG. 21a, the implant consists of two different materials.

An embodiment of the implant with an extensive coating formed around the implant, but almost exclusively on the ADLUMINAL side is illustrated in FIG. 22.

Figure 23:
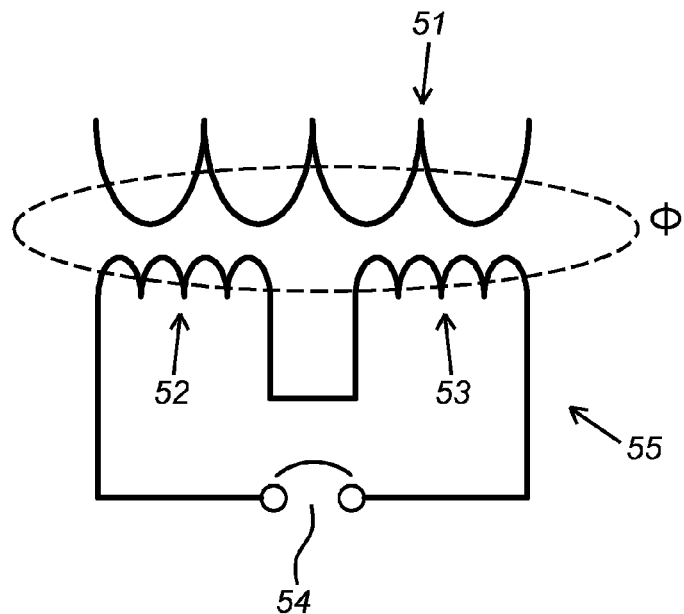

FIG. 23 illustrates the concept of the present invention whereby an implant device is provided with a built-in thermal switch.

Figure 24:
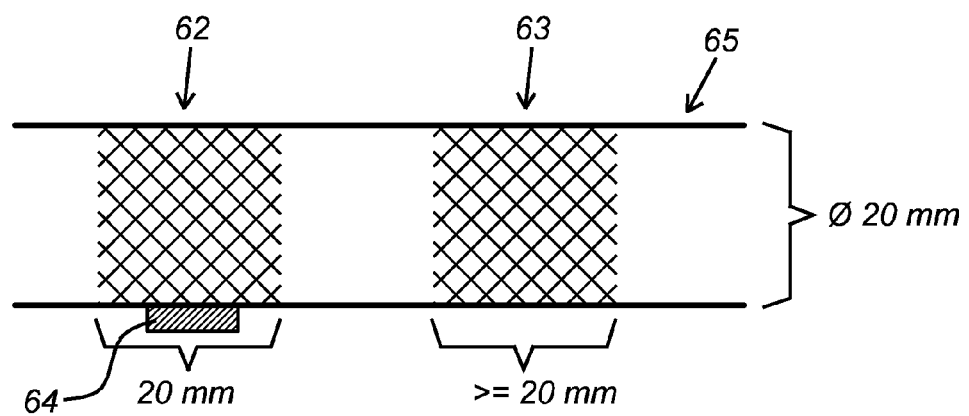

FIG. 24 illustrates the dimensions of an implant in an expanded position in a vessel.

FIGS. 25a-g illustrate different embodiments of the present invention, whereby the shape and absolute and relevant sizes of the coils may differ between different embodiments.

Figure 26:
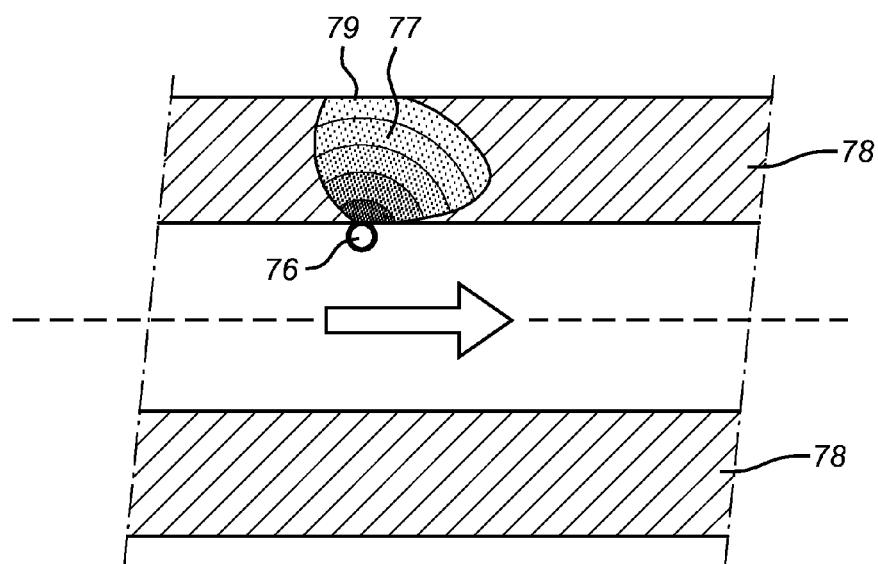

FIG. 26 illustrates that the heat is deposited mainly near the winding, but that it is possible that also the outer side of the vessel can be heated to an increased temperature.

Figure 27A:
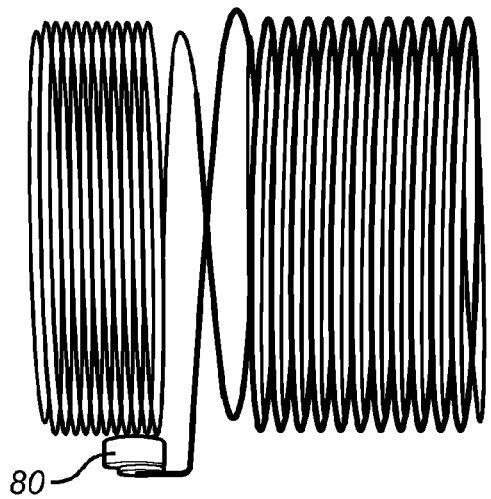
Figure 27B:
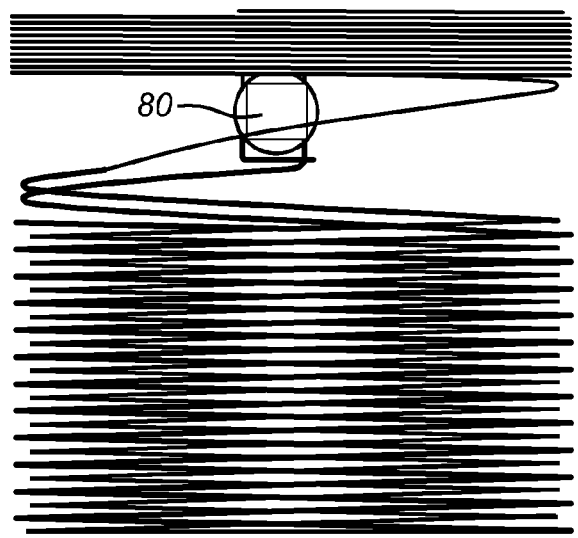

Further embodiments comprising e.g. a PTC or thermistor switch, are illustrated in FIGS. 27a-b for essentially cylindrical implants.

Figure 28:
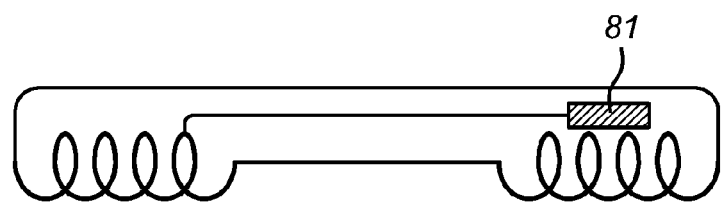

An AC-DC converter may be part of a larger electronic circuit which can be attached to a pcb and coupled to the coils as illustrated in FIG. 28.

FIGS. 29a-f illustrate electronic circuits which can be used in embodiments of the implant of the present invention.

FIGS. 30a-34 illustrate embodiments of external energy providing means which can be used in a system or method of the present invention for providing energy to the implant by providing a time-varying magnetic field at the position of the implant.

DETAILED DESCRIPTION OF THE INVENTION

The present invention concerns a system of one or more implant devices and excitation device, an implant device and a method using the system and one or more devices for the treatment of arterial and venous structures. The present invention also concerns implant devices, a system of implant devices and external excitation means, and a method for positioning one or more implant devices in a vessel, and subsequently heating these implant devices, preferably simultaneously, thereby transferring heat from implant devices to the vessel's inner wall.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The expressions "implant" and "implant device" are used interchangeably in this application. An implant device as used in the present context, refers to an artificial tube or tube-like device, i.e. a device which has a circumferential wall and which is at least partly open at the top and at the bottom, whereby said circumferential wall may or may not have openings or holes, said tube or tube-like device intended to be placed inside a vessel of the body of a patient, e.g. a vein, or inside a vessel of a human or animal corpse or model of a human or animal body. In the present context, the terms "implant" and "implant device" do not necessarily mean that the device is placed inside a vessel to keep this vessel open for fluids, although this can be one of the effects of the device. The implant device is, however, meant to be seated in a fixed position compared to the vessel and not to move due to fluid flow through the vessel. When using the term "implanted" device, it is meant that the implant or implant device has been implanted. In an embodiment, the implant device is a stent device, meaning that the device has the intended effect of keeping the vessel open for fluids when implanted.

The terms "catheter" and "sheath" are used interchangeably in this application.

The term "guidewire" is used in this application for a device which can be controllably guided when inserted into a body. In a preferred embodiment, it is a catheter, i.e. a guiding catheter. In another embodiment, it is solid and does not have a lumen.

The terms "Curie temperature" and "Néel temperature" refer to the temperature above which ferromagnetic, antiferromagnetic and ferrimagnetic materials become para- or diamagnetic, and are used interchangeably in the following.

"Resistive heating" and "Joule heating" here and throughout this text are used as synonyms and refer to the process by which the passage of an electric current through a conductor releases heat.

"Thermal switch" and "temperature-controlled switch" here and throughout this text are used as synonyms and refer to a switch capable of closing or opening one or more electrical circuits, depending on the value of a temperature. This temperature may be the temperature at the position of the switch, or may be the temperature as obtained on a different position. Specific embodiments of thermal switches are presented further in this text.

In a first aspect, the present invention provides a system for ablation of at least a part of a vessel's wall from the inside, comprised of
  a self-expanding implant device, adapted to be implanted and deployed within said vessel; whereby said implant comprises an ablation region along at least a portion of its length, said ablation region being adapted for surface contact with said vessel and said ablation region subtending at least a substantially complete circumferential band or a spiraling band and being effective to ablate a signal-blocking path within said vessel upon application of energy to the implant;
  external energy-providing means, which are spatially separated from the implant device and able to provide energy to the implant device for increasing the temperature of the ablation region of the implant device up to an ablation temperature.

The implant device is self-expanding, for example, being formed of a shape memory alloy, and is configured to lodge against the interior wall of e.g. a renal artery. The implant may be formed as a loop, helix, progressively wound helix or other suitable shape. It may have anchoring means such as hooks or barbs near the ends. The implant device may comprise an ablation region which is in contact with the ablation region of the vessel's wall. Preferably, the ablation region comprises a substantially complete circumferential band or a spiraling band around the vessel's wall, or a dotted, dashed or interrupted circumferential or spiraling band around the vessel's wall. The ablation region may comprise a complete circumferential band or a spiraling band around the vessel's inner wall, or the ablation region may comprise a complete circumferential band or a spiraling band around the vessel's wall and this for the complete thickness of the wall. With 'substantially' is meant that the ablation region is such that all electric signals arising at one side of the ablation region do not reach the other side, i.e. a signal-blocking path is ablated. Energy can be provided to the implant device by external means through electromagnetic radiation, through hysteresis heating via a time-varying magnetic field, by direct and indirect induction and by Joule heating, by acoustic, mechanical-vibrational and chemical energy means, by a thermal/chemical or mechanical/chemical release system.

One of the advantages of the present invention over prior art techniques, is that the one or more implant devices can be heated up simultaneously, i.e. the delivery of energy to the implants happens at the same time and does not need to be done sequentially. This saves time and increases the patient's comfort. Through built-in control of the temperature, e.g. by using magnetic material with a specified Curie temperature or by using the proper insulation material in the implant, additional energy delivery will not further increase the temperature built-up in the implant.

By 'external' energy-providing means is meant that these means are spatially separated from the implant device, i.e. there is no physical connection between the energy-providing means and the implant device, or, more specifically, the energy-providing means are completely outside the patient's body and the patient's skin can remain intact while the energy is provided.

The temperature of ablation region is specified according to the needs of the treatment. Depending on the ablation temperature needed, the implant device can be engineered to be warmer at certain regions than in other regions by using the magnetic and thermal properties of the materials of which the implant device is composed. In an embodiment, parts of the implant device may be thermally isolated from other parts of the implant device or from parts of the body or bodily fluids.

In a preferred embodiment, the system comprises more than one implant device, each of which adapted to be implanted and deployed within one or more vessels. These implant devices can each be adapted to be implanted and deployed within one or more renal arteries.

In a particular preferred embodiment, one or more implant devices of the system comprise a proximal portion having a first diameter and a distal portion having a second diameter that is less than the first diameter and that is sufficient to enable said implants to seat within one or more vessels.

In a particular preferred embodiment, one or more implant devices of the system comprise a proximal portion having a first diameter and a distal portion having a second diameter that is greater than or equal to the first diameter and that is sufficient to enable said implants to seat within one or more vessels.

It should be clear that the shape of the implant device can be adapted so as to fit into the specific vessel.

In order to make the shape and dimensions of the implants, it is possible by a scanning technique such as CT-scan or MRI, to collect data on the varying diameter of the vessel. From these data, one can derive the necessary shape and dimensions of the implants e.g. for all two renal arteries of a patient. Again this measuring can be done without a surgical procedure, thereby increasing the patient's comfort and wellbeing and reducing medical risks. After this measuring, the implants can be custom-made to fit the patient's vessel or vessels.

In a preferred embodiment, at least part of the one or more implant devices of the system is made from at least one material which shows magnetic hysteresis, such as a ferromagnetic, ferrimagnetic or anti-ferromagnetic material. Furthermore, the external energy-providing means may create a time-varying magnetic field at the position of the one or more implant devices. In a more preferred embodiment, this time-varying magnetic field is created by an electric coil through which a time-varying electrical current is sent.

Magnetic hysteresis arises in a plethora of materials. Most known and most used are the ferromagnetic, anti-ferromagnetic and ferrimagnetic materials. These have highly non-linear magnetic properties, i.e. the magnetic induction field is not directly proportional to the applied magnetic field inside the material. However, all these material lose their specific magnetic properties above a certain temperature, called the Curie or Néel temperature. This temperature is material-specific. Above this temperature, the ferromagnetic, anti-ferromagnetic and ferrimagnetic materials become para- or diamagnetic and thereby lose their non-linear magnetic properties. The non-linear magnetic properties of ferromagnetic, anti-ferromagnetic and ferrimagnetic materials can be deduced from the hysteresis that is observed when applying a time-varying magnetic field.

Magnetic hysteresis is observed in magnetic materials, such as ferromagnets. The main feature of ferromagnets is the presence of spontaneous magnetization. A ferromagnet usually is not uniformly magnetized but is divided into domains-regions of uniform spontaneous magnetization whose degree of magnetization (the magnetic moment per unit volume) is identical, although the directions are different. Under the effect of an external magnetic field the number and size of the domains magnetized along the field increase at the expense of other domains. Moreover, the magnetic moments of certain domains may rotate in the direction of the field. As a result the magnetic moment of the sample increases.

Figure 16:
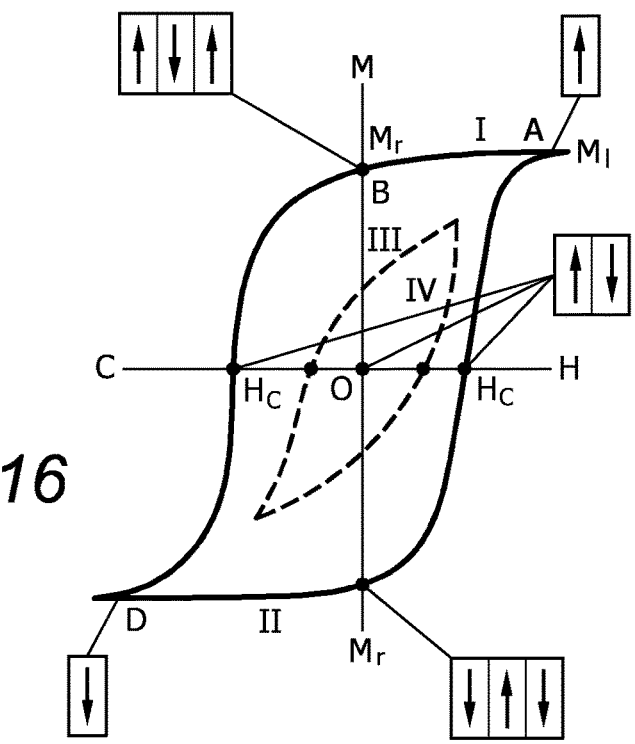
FIG. 16 shows a magnetic hysteresis loop for a ferromagnet: H is the intensity of the magnetic field, M is the magnetic moment of the sample, $H_c$ is the coercive field, $M_r$ is the residual magnetic moment, and $M_s$ is the saturation magnetic moment. The nonlimiting hysteresis loop is shown by the dotted line. The domain structure of the sample for certain points on the loop is shown schematically.

The dependence of the magnetic moment M of a ferromagnetic sample on the intensity H of the external magnetic field (the magnetization curve) is shown in FIG. 16. In a sufficiently strong magnetic field the sample is magnetized to saturation (as the field increases further, the value of M remains virtually unchanged—point A). Here the sample consists of one domain with a magnetic moment of saturation $M_s$ oriented along the field. As the intensity H of the external magnetic field is reduced, the magnetic moment M of the sample will decline along curve I primarily because of the appearance and growth of domains whose magnetic moment is oriented against the field. The growth of the domains is due to the movement of the domain walls. This movement is hindered by the presence in the sample of various defects (such as impurities or inhomogeneities) that strengthen the domain walls at some points; very strong magnetic fields are required to displace them. Therefore as the field H drops to zero, the so-called residual magnetic moment $M_r$ (point B) is retained. A sample can be completely demagnetized only in a sufficiently strong field of opposite direction, which is called a coercive field (coercive force) $H_c$ (point C). As the magnetic field of reverse orientation is further increased, the sample is once again magnetized along the field to saturation (point D). Magnetic reversal (from point D to point A) takes place along curve II. Thus, as the field undergoes a cyclical change, the curve characterizing the change in the magnetic moment of the sample forms a magnetic hysteresis loop. If the field H changes cyclically with such limits that magnetization does not reach saturation, a nonlimiting magnetic hysteresis loop is produced (curve III). By reducing the extent of the change in field H to zero, the sample can be completely demagnetized (point O can be reached). The magnetization of the sample from point O proceeds along curve IV.

In magnetic hysteresis different values of the magnetic moment M correspond to the same value of the external magnetic field intensity H. This nonuniqueness is due to the influence of the states of the sample that precede the given state (that is, to the magnetic prehistory of the sample).

The shape and size of magnetic hysteresis loops and the quantity $H_c$ may range within wide limits in various ferromagnets. For example, in pure iron, $H_c=1$ oersted, and in a magnico alloy $H_c=580$ oersteds. A magnetic hysteresis loop is strongly affected by processing of the material, during which the number of defects is changed. The area of a magnetic hysteresis loop is equal to the energy lost in the sample in one cycle of field change. This energy is also proportional to the total volume of ferromagnetic material in the sample. This energy ultimately is used to heat the sample. Such energy losses are called hysteresis losses. In cases when losses to hysteresis are undesirable (for example, in transformer cores and in the stators and rotors of electrical machinery), magnetically soft materials with a low $H_c$ and a small hysteresis loop area are used. On the other hand, magnetically hard materials with a high $H_c$ are required to manufacture permanent magnets.

As the frequency of the alternating magnetic field (the number of magnetic reversal cycles per unit time) increases, other losses caused by eddy currents and magnetic viscosity are added to hysteresis losses. At high frequencies the area of the hysteresis loop increases correspondingly. Such a loop is sometimes called a dynamic loop, in contrast to the static loop described above.

Many other properties of a ferromagnet, such as electrical resistance and mechanical deformation, depend on the magnetic moment. A change in magnetic moment also brings about a change in these properties—for example, galvanomagnetic and magnetostrictive hysteresis, respectively, are observed.

Figure 17:
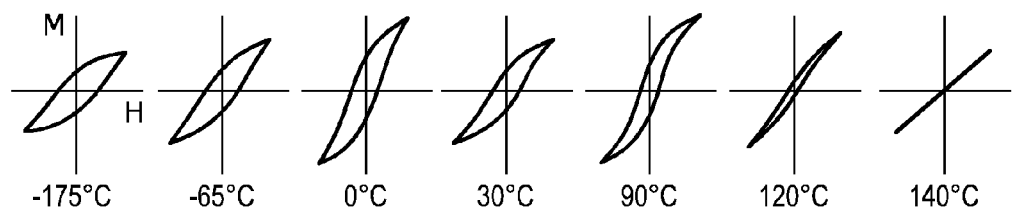
FIG. 17 shows the typical temperature dependence of the hysteresis loop of a magnetic material with Curie or Néel temperature of 140° C.

The hysteresis loop depends on the temperature. FIG. 17 shows the typical temperature dependence of the hysteresis loop of a magnetic material with Curie or Néel temperature of 140° C. Note that only the temperature dependence of the shape is characteristic and no units are given on the axes, the figure is meant for illustration purposes. It is observed that the hysteresis loop changes with temperature, becoming sharper and thinner, and eventually disappearing at the Curie or Néel temperature. From this temperature onwards, the material becomes para- or diamagnetic and no heating losses due to hysteresis are observed. This means that the material does not heat up anymore, at least not due to hysteresis effects, and remains at the Curie or Néel temperature. (In the following, the two terms 'Curie' and 'Néel' temperature can be used interchangeably.) It should be remarked that heating due to other effects, such as direct or indirect induction may still be possible, but these effects are negligible in the present case, especially when compared to the gigantic heating capabilities by hysteresis effects.

It should be now clear to the skilled person that when the ablation region of an implant device comprises material with Curie temperature of e.g. 40° C., the implant will be heated up to this temperature and not more when being subjected to a time-varying magnetic field, e.g. by the external energy-providing means of the system of the present invention. If the ablation temperature needs to be 42° C. or 45° C., the magnetic material used in the implant may be altered to have this temperature as Curie temperature. This can be done by e.g. changing the composition of an alloy of magnetic material. The Curie temperature of a magnetic material can be very precisely engineered.

In a preferred embodiment, the magnetic materials used in the implant device are a combination or alloy of the following materials: MnAs, Gd, Gd with a thin Fe overlayer, Ni—Fe alloy with around 29.5 at. % Ni which is cooled slowly from 1000° C., Ni—Fe with 30 at. % Ni, Cr, CoO, $ZnFe_2O_4$, are any magnetic material with Curie or Néel temperature above 10, 20, 25, 30, 35, 40° C. and/or below 75, 70, 65, 60, 55, 50, 45, 40° C.

The Curie or Néel temperatures of alloys or composite materials can depend highly on the procedure for making these materials. Especially annealing procedures may be important. Also other ways of altering the Curie temperatures such as ion radiation can be used to provide the desired material. One can use any magnetic material, alloy, binary alloy, ternary alloy or quaternary alloy with the desired Curie or Néel temperature as specified in standard reference works such as the Landolt-Börnstein database.

In another embodiment, the system also comprises
a sheath suitable for transporting and delivering the one or more implant devices to or near the desired position in the one or more vessels;
a guidewire suitable for sequentially guiding the sheath with the one or more implants to the desired position in the one or more vessels.

Figure 12:
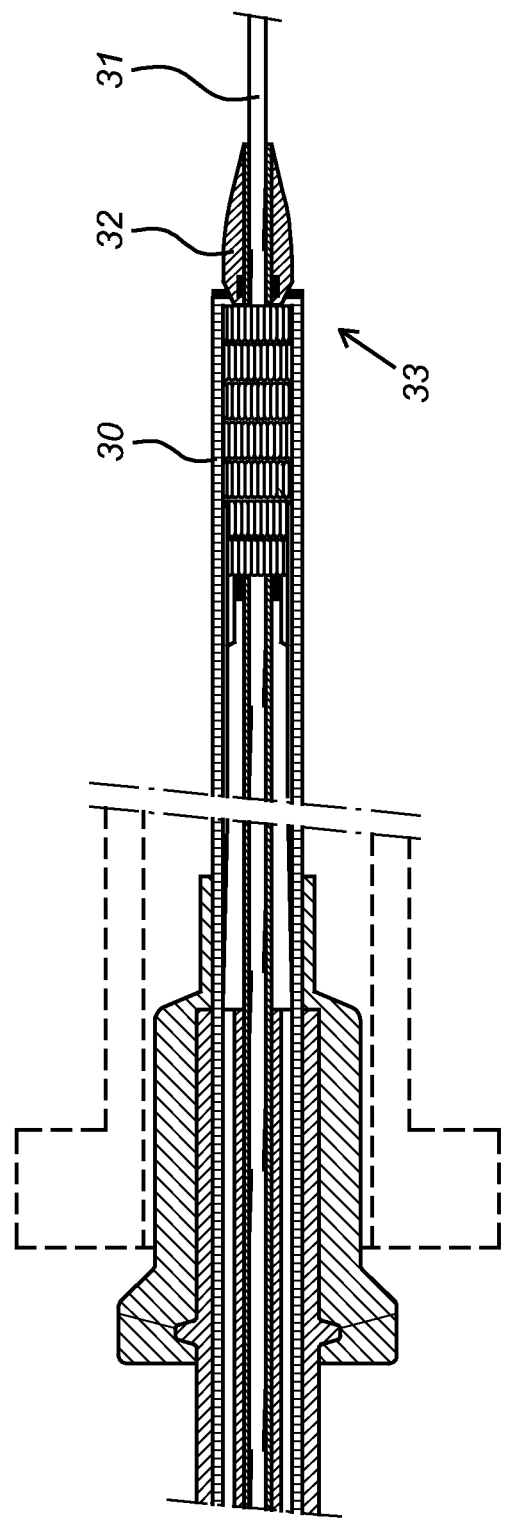
FIG. 12 schematically represents an embodiment of a sheath with guidewire and implant device.

The sheath in this embodiment includes an implant delivery system capable of delivering the one or more implant devices as described in this text. An embodiment of such sheath with delivery device and guidewire is shown in FIG. 12.

In a further aspect, the present invention provides a self-expanding implant device adapted to be implanted and deployed within a vessel; said implant comprising an ablation region along at least a portion of its length, the ablation region being adapted for surface contact with the vessel and the ablation region subtending at least a substantially complete circumferential band or a spiraling band and being effective to ablate a signal-blocking path within the vessel upon application of energy to the implant; whereby said ablation region comprises at least one material which shows magnetic hysteresis, such as a ferromagnetic, ferrimagnetic or anti-ferromagnetic material.

Preferably said material comprises a ferrous fluid, i.e. ferromagnetic, ferrimagnetic and/or anti-ferromagnetic particles suspended in a heat conducting fluidum, whereby said material is preferably contained within said implant device. In a more preferred embodiment, said implant device comprises one or more fluid-tight cavities comprising said ferromagnetic, ferrimagnetic and/or anti-ferromagnetic particles in said heat conducting fluidum. In an even more preferred embodiment, said particles comprise any or any combination of the following materials: $SrFe_{12}O_{19}$, $Me_a$-2W, $Me_a$-2Y, and $Me_a$-2Z, wherein 2W is $BaO:2Me_aO:8 Fe_2O_3$, 2Y is 2 ($BaO:Me_aO:3 Fe_2O_3$), and 2Z is 3 $BaO: 2Me_aO:12Fe_2O_3$, and wherein $Me_a$ is a divalent cation, whereby the divalent cation is preferably selected from Mg, Co, Mn and Zn, and/or $1Me_bO:1Fe_2O_3$, where $Me_bO$ is a transition metal oxide selected from Ni, Co, Mn, and Zn, and/or metal alloys such as $La_{0.8}Sr_{0.2}MnO_3$, $Y_3Fe_{5-x}M_xO_{12}$ where M is Al, or Gd and $0<x<2$, and/or metal alloys of any combination of Pd, Co, Ni, Fe, Cu, Al, and Si and/or metal alloys of any combination of Gd, Th, Dy, Ho, Er, and Tm with any combination of Ni, Co, and Fe and/or metal alloys $RMn_2X$ where R is a rare earth, such as La, Ce, Pr, or Nb and X is either Ge or Si. Particularly preferred is any or any combination of the following alloys: NiCu with 28% or 29.6% Ni, NiPd, PdCo with 6.15% Pd, NiSi with 4% Ni, $(Ni,ZnO)Fe_2O_3$, $La_{0.8}Sr_{0.2}MnO_x$, $Y_3Fe_{5-x}Al_xO12$ with $1.0 \leq x \leq 1.7$. The particles can be of any size, preferably longer than 10 nanometers, more preferably longer than 20 nanometers in the longest dimension, and smaller than 500 micrometers, preferably smaller than 100 micrometers in the longest dimension. In certain embodiments, said particles are smaller than 1 micrometer, preferably smaller than 200 nanometers in the longest dimension. In other embodiments, said particles are longer than 1 micrometer, preferably longer than 20 micrometer in the longest dimension. Preferably said fluidum in which said particles are suspended comprises optimal heat conduction properties. In a preferred embodiment, said fluidum comprises a large heat capacity. In another preferred embodiment, said fluidum comprises a low heat capacity. The exact nature, amount and combination of which magnetic materials to use for the particles and which fluidum to use, depends on the desired temperature and heat for e.g. inducing complete spiral ablation of the inner wall of a renal artery. In a preferred embodiment, said magnetic materials comprise a Curie or Néel temperature of 37, 38, 39, 40, 41, 42, 43, 44, 45, 46, 47, 48, 49, 50, 51, 52, 53, 54, 55° C. or any value in between or any combination thereof, preferably said Curie or Néel temperature is smaller than 75° C., more preferably smaller than 70° C., even more preferably smaller than 65° C., yet more preferably smaller than 62° C., still more preferably smaller than 59° C., yet even more preferably smaller than 57° C., still even more preferably smaller than 55° C.

In a preferred embodiment, the implant device is adapted to be implanted and deployed within a renal artery.

In a particular preferred embodiment, parts of the implant device are made from more than one material showing magnetic hysteresis and which have different Curie or Néel temperatures.

Different temperatures cause different lesions on different places depending on which ablation regions of the implant device comprises which material. By thermally isolating parts of the implant device which consist of material with different Curie temperatures, a gradation in ablation temperature along the implant device is possible. Also, parts comprising material with higher heat capacities will heat up more slowly, but will remain hot longer afterwards, etc.

Engineering of ablation characteristics can be done by engineering the implant making use of the magnetic and thermal properties of the materials used in the implant.

In a more preferred embodiment the implant device is suitable for long-term implantation. In another embodiment, the implant device is a bio-resorbable implant device or an implant that disappears, e.g. by evaporation, after one or more ablation procedures. In a preferred embodiment, the implant device may comprise a proximal portion having a first diameter and a distal portion having a second diameter that is less than the first diameter and that is sufficient to enable said implant device to seat within a vessel. The implant device may further comprise anchoring means at or near the proximal or distal portion of said implant device, said anchoring means being suitable for keeping the device at or near the same position compared to the vessel's inner wall. The anchoring means may comprise hooks or barbs or anything else known in the art for keeping an implant device at the desired position.

In a preferred embodiment, the implant device comprises an elastically compressible body comprising externally triggerable portions and provided of anchoring means. The body may be mainly made of wires and may, in expanded or released position, be provided of a narrowing tubular shape and/or a somewhat flattened narrowing tubular shape, i.e. that the cross sections at most positions along the longitudinal axis are oval or round-shaped or the like, suitable to be placed inside a renal artery. The body may also comprise between two and five circular wires, a first bigger circular or oval wire, and further circular or oval wires with decreasing diameter, positioned and maintained at a distance from each other, at least when the body is in a released or not compressed position. The body may be built up out of braided metal wires (that have multiple interconnections, crossings and/or layers which allows for numerous connections with the vascular or arterial wall of the vessel). The body may be conceived as a spirally shaped wire of which the diameter gradually goes down along its longitudinal axis. The windings of the implant device may be mutually connected with bridging upstanding wire portions providing closed loops to ensure full and circular coverage of for example the renal arteries once the device is released. The body may show longitudinal metal beads that are outward bending, and that still show several interconnections between them, to ultimately form a metal cage. The implant device may be characterized in that the greatest distance between two points that can be measured on the circular or oval wires of the body will range from 3 to 30 mm, more specifically from 5 mm to 20 mm, even more specifically from 9 mm to 13 mm, if to be implanted in the renal artery. The implant device may be characterized in that the greatest distance between two points that can be measured on the circular or oval wires of the body of the implant device will range from 5 to 50 mm, more specifically from 8 mm to 40 mm, even more specifically from 10 mm to 30 mm, if to be implanted in the vessel. The body of the implant device may be mainly made of one or more metal alloys. The body of the implant device may comprise portions which are externally triggerable by means of an energy field or a combination of energy fields chosen from electromagnetic radiation, direct or indirect induction, acoustic energy, mechanical vibration, heating and/or changing other characteristics of the implant or portions thereof. Some of the material used in the implant device may be of the type that reacts, for example heats, in response to a remote applied alternating magnetic field. Energy can be provided to the implant device by external means through electromagnetic radiation, through hysteresis heating via a time-varying magnetic field, by direct and indirect induction and by Joule heating, by acoustic, mechanical-vibrational and chemical energy means, by a thermal/chemical or mechanical/chemical release system. The body may comprise portions made of different metal alloys with optionally different ferromagnetic properties and/or absorption coefficients, with specific response to alternating magnetic fields. Portions of the body of the implant device may be provided of one or more coatings with varying properties. The wire or wires or other portions of the body of the implant device is/are composed of different layers made of different alloys and/or of other materials. The implant device may be further characterized in that different coatings or layers represent different responses to externally applied energy fields, for example to externally applied alternating magnetic fields. An adluminal coating or layer with high isolation characteristics may be provided to the implant device. The body of the implant device may have self-expanding properties thanks to the elastic characteristics of the material used, and thanks to the geometry of the body, and further expansion is stopped when it encounters a counter pressure of about 10 to 40, preferably 20 to 30, more preferably 22 to 28, even more preferably around 25 mm Hg, equal to the distension pressure needed to alter the vessel's anatomy. The implant device may be characterized in that it is provided of toxic substances that are only released upon introduction into the renal artery, for example after applying an external energy field, which toxic substances then produce a lesion of limited necrosis/neurotoxicity. These toxins may include, but are not limited to ethanol, tetrodotoxin and batrachotoxin, maurotoxin, agitoxin, charybdotoxin, margatoxin, slotoxin, scyllatoxin and hefutoxin, calciseptine, taicatoxin, calcicludine, and PhTx3, botulinum toxine, cytochalasin D, rapamycin, sirolimus, zotarolimus, everolimus, paclitaxel, glutamate, isoquinoline, N-methyl-(R)-salsolinol, Beta-carboline derivates. The implant device may be provided of micro pores wherein substances are provided, which can be released by a triggering energy field. The implant device may be provided of a thermoactive coating which is only activated upon temperatures above 35° C. so that the body temperature would trigger activation. The implant device may be provided of a thermoactive coating which is only activated upon temperatures above 45° C. so that an external application of an energy field would trigger activation. The implant device may be provided of anchoring means which mainly consist of the elongated shape and/or the expanding forces optionally in combination with the wired structure allowing partial insertion or impression in the wall of the vessel, e.g. of the renal arteries. These anchoring means may also comprise hooks or barbs or the like, optionally provided on the outwardly directed portions of the implant.

In a preferred embodiment, said implant device comprises cavities which are filled with one or more substances and which open when the implant is heated and/or which open when the implant acquires body temperature, and/or whereby said implant comprises a coating comprising one or more substances.

In a preferred embodiment, an implant device according to the present invention comprises a maximal circumference and a minimal circumference and a ratio between maximal and minimal circumference, whereby said ratio is smaller than 10, preferably smaller than 9, more preferably smaller than 8, even more preferably smaller than 7, yet more preferably smaller than 6 and larger than 1.1, preferably larger than 1.5, more preferably larger than 2, even more preferably larger than 2.5, yet more preferably larger than 3. In a preferred embodiment, the implant device comprises a variable circumference along a longitudinal direction of the implant, said circumference varying between at least 20 mm, preferably at least 25 mm, more preferably at least 30 mm, even more preferably at least 36 mm, yet more preferably at least 42 mm, still more preferably at least 48 mm and at most 375 mm, more preferably at most 350 mm, even more preferably at most 325 mm, yet more preferably at most 300 mm, still even more preferably at most 275 mm, yet even more preferably at most 250 mm. Such a ratio or dimension may be necessary to ensure that an essentially circumferential or spiraling band of the vessel's inner wall would be subtended, in particular if the vessel is a renal artery.

In a particularly preferred embodiment, said circumference may be at most 200%, preferably at most 190%, more preferably at most 180%, even more preferably at most 170%, yet more preferably at most 160%, still more preferably at most 150% of the original diameter of the vessel for which the implant device is adapted, e.g. of the renal artery, etc. when the self-expanded implant device is in an expanded state.

In a preferred embodiment, the implant device comprises an outer surface comprising zig-zag or woven or braided material, drawn tubes, eccentrically drawn tubes, hollow struts, hollow struts filled with fluid, or any combination thereof.

In a preferred embodiment, an implant device according to the present invention comprises an essentially cylindrical shape preferably comprising a diameter which is at least 2 mm, preferably at least 3 mm, more preferably at least 4 mm, even more preferably at least 5 mm, yet more preferably at least 6 mm and at most 20 mm, preferably at most 16 mm, more preferably at most 13 mm, even more preferably at most 10 mm, yet more preferably at most 9 mm. Such a shape or dimension may be necessary to ensure that a circumferential or spiraling band of the vessel's inner wall would be subtended, in particular in an essentially cylindrical portion of said vessel, in particular if the vessel is a renal artery.

In a preferred embodiment, an implant device according to the present invention comprises a distal portion and a proximal portion, whereby said ablation region is located within 50%, preferably within 40%, more preferably within 30% of the implant's total length from the proximal portion. In a preferred embodiment, an implant device according to the present invention comprises a distal portion and a proximal portion, whereby said ablation region is located within 25 mm, preferably within 20 mm, more preferably within 15 mm from the proximal portion.

In a preferred embodiment, the implant device comprises a distal portion and a proximal portion, and comprising an anchoring device connected to the ablation region of said implant via a thermally insulating connection for preventing overheating of said anchoring device, preferably whereby said anchoring device is connected to the distal portion. The anchoring device may comprise different material than the rest of the implant device. In particular, the anchoring device may have different thermal characteristics due to its dimensions, shape or material. The anchoring device may be connected to the distal portion of the implant device in order to have optimal anchoring in e.g. the lumen of a renal artery. The thermally insulating connection may comprise thermally insulating material, or its shape and dimensions may increase thermal insulation, e.g. a number of thin straps or wires attaching the anchoring device to the ablation region.

In a preferred embodiment, the system for the treatment of arterial and venous structures, comprises an implant device according to any of the above embodiments and an excitation or energy-providing device preferably conceived to be used from the exterior of the patient, after being provided of an implant device, whereby the excitation serves to change the characteristics of the implant device in order to treat the arterial or venous structure where the implant device is located. The excitation device for the treatment of arterial and venous structures, may be conceived to be used in cooperation with an implant device according to any embodiment described in this text.

In a preferred embodiment the part of the implant device which can come into contact with the patient's blood when said implant device is implanted, is thermally isolated from the rest of the implant device such that the blood is not heated or overheated during the excitation of the implant device. Such part may comprise an adluminal coating or a layer with high isolation characteristics. It is clear that heating of the blood should be avoided as much as possible for the benefit and comfort of a patient.

In another embodiment, the implant device comprises a core region of material with a certain Curie temperature, surrounded by other material with thermal and/or elastic properties suitable for the implant device's purpose. As such, one can engineer the temperature profile through the implant device. It should be clear that the parts of the implant which are meant to contact the vessel wall and the form lesions by ablation, should be heated mostly while other parts of the implant, which are in contact with the vessel or the blood and are not meant to form lesions, should receive as little heat as possible for the wellbeing of a patient.

In still another embodiment, the implant device comprises cavities which are filled with one or more substances and which open when the implant is heated. In a preferred embodiment, these substances are mixed before being released into the patient's body or vessel wall, e.g. to deliver a two-component neurotixine. In a more preferred embodiment, these substances are a selection or a composition of one or more of the following substances:
- ethanol;
- tetrodotoxin and batrachotoxin;
- maurotoxin, agitoxin, charybdotoxin, margatoxin, slo-toxin, scyllatoxin or hefutoxin;
- calciseptine, taicatoxin, calcicludine, or PhTx3;
- botulinum toxide;
- cytochalasin D, rapamycin, sirolimus, zotarolimus, everolimus, paclitaxel;
- glutamate;
- isoquinoline;
- N-methyl-(R)-salsolinol;
- Beta-carboline derivates.

With such implants, it becomes possible to release the desired substances into the vessel wall or the blood stream at the desired moment, by heating the implant with e.g. external energy providing means. Furthermore, the implant and cavities in the implant may be designed such that the two components of e.g. a two-component neurotixine, are mixed before being released into the body.

In a preferred embodiment, an implant device according to the present invention comprises one or more deposits of toxin, preferably on an outer surface of said device, said deposits covered by a metal layer capable of being resolved by heating, preferably hysteresis heating.

In a similar aspect, the present invention provides an implant comprising an electrical circuit comprising a pickup coil, a heater coil and a temperature-controlled switch which comprises a closed position and an interrupted position. Said switch preferably comprises a bi-metallic component and/or a thermistor, such as a PTC thermistor and/or said switch preferably comprises a temperature sensor and a, preferably digital, thermostat connected to said sensor and to said switch for interrupting said switch and thus said electrical circuit when said sensor measures a pre-determined temperature. Preferably said switch is arranged to change from said closed to said open position when a temperature at or near said implant is higher than a pre-defined ablation temperature. In a preferred embodiment, said switch is arranged to change from said open to said closed position when a temperature at or near said implant is lower than a pre-defined switching temperature. In one embodiment, said ablation temperature is equal to said switching temperature. In another embodiment, said switching temperature is different from said ablation temperature, preferably said switching temperature is lower than said ablation temperature, e.g. at least 0.01° C., 0.1° C., 0.5° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C. lower than said ablation temperature. In a preferred embodiment, said circuit comprises more than one switch, e.g. 2, 3, 4 or more switches, preferably connected in series, for redundancy, i.e. for ensuring at least one switch functions as desired.

In yet another similar aspect, the present invention provides an implant for treating arterial hypertension by blocking renal sympathetic nerve signals via ablation by heating, comprising an electrical circuit comprising a pickup coil, a heater coil and a temperature-dependent LC-circuit, whereby said LC circuit comprises a resonant frequency which is temperature-dependent.

The pickup coil of the above implants is arranged for inducing an electrical current through an electrical circuit to which it is connected, under the influence of a time-varying magnetic flux through said pick-up coil. Thereto, said pickup coil preferably comprises a low resistance and a high inductance.

Preferably, said pickup coil comprises a resistance which is larger than 0.02 Ohm, preferably larger than 0.05 Ohm, more preferably larger than 0.1 Ohm, even more preferably larger than 0.15 Ohm, yet more preferably larger than 0.2 Ohm, still more preferably larger than 0.3 Ohm, still even more preferably larger than 0.5 Ohm, and/or smaller than 30 Ohm, preferably smaller than 30 Ohm, more preferably smaller than 25 Ohm, even more preferably smaller than 20 Ohm, yet more preferably smaller than 15 Ohm, still more preferably smaller than 10 Ohm, yet even more preferably smaller than 5 Ohm, most preferably about 1 Ohm.

Preferably, said pickup coil comprises an inductance which is larger than 0.02 µH, preferably larger than 0.05 µH, more preferably larger than 0.1 µH, even more preferably larger than 0.15 µH, yet more preferably larger than 0.2 µH, still more preferably larger than 0.3 µH, still even more preferably larger than 0.5 µH, and/or smaller than 30 µH, preferably smaller than 30 µH, more preferably smaller than 25 µH, even more preferably smaller than 20 µH, yet more preferably smaller than 15 µH, still more preferably smaller than 10 µH, yet even more preferably smaller than 7 µH, most preferably about 4 µH, e.g. 1 µH, 2 µH, 3 µH, 4 µH, 5 µH, 6 µH, 7 µH, or any value therebetween.

In a preferred embodiment, said heater coil is arranged for subtending a substantially complete circumferential or a spiraling ablation region in a vessel, preferably in a renal artery, for obtaining a substantially complete circumferential or spiraling signal-blocking lesion on the inner wall of said vessel. Preferably said heater coil comprises a high resistance and a low inductance.

Preferably, said heater coil comprises a resistance which is larger than 0.4 Ohm, preferably larger than 1 Ohm, more preferably larger than 2 Ohm, even more preferably larger than 3 Ohm, yet more preferably larger than 4 Ohm, still more preferably larger than 6 Ohm, still even more preferably larger than 10 Ohm, and/or smaller than 150 Ohm, preferably smaller than 100 Ohm, more preferably smaller than 80 Ohm, even more preferably smaller than 60 Ohm, yet more preferably smaller than 50 Ohm, still more preferably smaller than 40 Ohm, yet even more preferably smaller than 30 Ohm, most preferably about 25 Ohm.

Preferably, said heater coil comprises an inductance which is larger than 0.02 µH, preferably larger than 0.05 µH, more preferably larger than 0.1 µH, even more preferably larger than 0.15 µH, yet more preferably larger than 0.2 µH, still more preferably larger than 0.3 µH, still even more preferably larger than 0.5 µH, and/or smaller than 30 µH, preferably smaller than 30 µH, more preferably smaller than 25 µH, even more preferably smaller than 20 µH, yet more preferably smaller than 15 µH, still more preferably smaller than 10 µH, yet even more preferably smaller than 7 µH, most preferably about 4 µH, e.g. 1 µH, 2 µH, 3 µH, 4 µH, 5 µH, 6 µH, 7 µH, or any value there between.

In a particular preferred embodiment, the resistance of the heater coil is larger than the resistance of the pickup coil and/or the inductance of the pickup coil is larger than the inductance of the heater coil.

In a preferred embodiment, the current flowing through the heater coil, when the implant is activated e.g. by external energy-providing means such as by an imposed time-varying magnetic field via inductance, is larger than 0.1 A, preferably larger than 0.2 A, more preferably larger than 0.3 A, even more preferably larger than 0.4 A, yet more preferably larger than 0.5 A, still more preferably larger than 0.6

A, yet even more preferably larger than 0.7 A, still even more preferably larger than 0.8 A, and smaller than 10 A, more preferably smaller than 8 A, even more preferably smaller than 6 A, yet more preferably smaller than 4 A, still more preferably smaller than 2 A, yet even more preferably smaller than 1.5 A, still even more preferably smaller than 1 A, most preferably about than 0.9 A.

The pre-determined temperature in the present invention is preferably an ablation temperature for the inner wall of a vessel into which the implant is to be placed. Preferably said ablation temperature is 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75° C. or any value in between.

In a preferred embodiment, said pick-up coil, said heater coil and said temperature-controlled switch comprising said bi-metallic component are connected in series, whereby said bi-metallic component is in an open position when heated above a pre-defined temperature, thereby interrupting said circuit and stopping the heater coil from heating up, and whereby said bi-metallic component is in a closed position when its temperature is below said temperature, thereby closing said circuit such that a current, e.g. an induced current, can flow through the heater coil.

Preferably said implant comprises a circuit supply coil capable of picking up an AC current via induction from an externally applied time-varying magnetic field, said supply coil coupled to an AC-DC converter for providing a DC current or voltage, preferably to said switch or to other electronic components of said implant.

In a preferred embodiment, the implant comprises a source electrical circuit and a heating electrical circuit, which can be separately closed and/or open, whereby said source electrical circuit is arranged for providing a DC voltage and/or current output from an induced AC current in said pick-up loop. Preferably said DC output is connected to said switch for providing said switch with energy. Preferably said heating electrical circuit is arranged for heating said heater coil via resistive heating when said switch is closed, thereby allowing a heating current to flow through said heater coil.

In a preferred embodiment, said pickup coil and said heater coil are connected in series when said switch is closed, thereby allowing an electrical current picked up by induction by said pickup coil to flow through said heater coil, thereby heating said heat coil through resistive heating.

Preferably said heating current comprising an AC current, which may be induced in said pick-up coil and transferred to said heater coil if said switch is closed, and/or said AC current may be induced in said heater coil by external energy providing means such as an external generator. Said heating current may comprise a DC current, e.g. a DC current as provided for by a supply coil coupled to an AC-DC convertor.

In a preferred embodiment, said implant is at least partly self-expanding. In a preferred embodiment, said implant comprises a cylindrical shape for implantation into a renal artery.

Preferably, said pickup coil comprises a length which is larger than 10 mm, more preferably larger than 12 mm, even more preferably larger than 14 mm, yet more preferably larger than 15 mm, still more preferably larger than 16 mm, yet still more preferably larger than 17 mm, yet even more preferably larger than 18 mm, still even more preferably larger than 19 mm, most preferably larger than 20 mm, and smaller than 95 mm, more preferably smaller than 90 mm, more preferably smaller than 85 mm, even more preferably smaller than 80 mm, yet more preferably smaller than 75 mm, still more preferably smaller than 70 mm, yet still more preferably smaller than 65 mm, yet even more preferably smaller than 60 mm, still even more preferably smaller than 55 mm, most preferably smaller than 50 mm.

Preferably, said pickup coil comprises a maximal diameter which is larger than 10 mm, more preferably larger than 12 mm, even more preferably larger than 15 mm, yet more preferably larger than 18 mm, still more preferably larger than 20 mm, yet still more preferably larger than 22 mm, yet even more preferably larger than 24 mm, still even more preferably larger than 26 mm, most preferably larger than 28 mm, and smaller than 70 mm, more preferably smaller than 65 mm, even more preferably smaller than 60 mm, yet more preferably smaller than 50 mm, still more preferably smaller than 40 mm, yet still more preferably smaller than 35 mm, yet even more preferably smaller than 30 mm, still even more preferably smaller than 25 mm, most preferably smaller than 20 mm when said implant is in an expanded position.

Preferably, said heater coil comprises a length which is larger than 1 mm, more preferably larger than 2 mm, even more preferably larger than 3 mm, yet more preferably larger than 4 mm, still more preferably larger than 5 mm, most preferably larger than 6 mm, and smaller than 30 mm, more preferably smaller than 27 mm, still more preferably smaller than 25 mm, yet even more preferably smaller than 24 mm, still even more preferably smaller than 22 mm, most preferably smaller than 20 mm.

Preferably, said heater coil comprises a maximal diameter which is larger than 2 mm, more preferably larger than 4 mm, even more preferably larger than 6 mm, yet more preferably larger than 8 mm, still more preferably larger than 10 mm, yet still more preferably larger than 12 mm, yet even more preferably larger than 13 mm, still even more preferably larger than 14 mm, most preferably larger than 15 mm, and smaller than 90 mm, more preferably smaller than 80 mm, even more preferably smaller than 70 mm, yet more preferably smaller than 60 mm, most preferably smaller than 50 mm when said implant is in an expanded position.

Preferably, said implant comprises a distance between said pickup coil and said heater coil, said distance being larger than 1 mm more preferably larger than 3 mm, even more preferably larger than 5 mm, yet more preferably larger than 6 mm, still more preferably larger than 7 mm, yet still more preferably larger than 8 mm, yet even more preferably larger than 9 mm, still even more preferably larger than 10 mm, most preferably larger than 12 mm, and smaller than 80 mm, more preferably smaller than 70 mm, even more preferably smaller than 60 mm, yet more preferably smaller than 50 mm, most preferably smaller than 40 mm.

The present invention further provides a system for treating arterial hypertension by blocking renal sympathetic nerve signals via ablation by heating, comprising an implant comprising an electrical circuit comprising a pickup coil, a heater coil and a temperature-controlled switch as described in this text, and a magnetic field generator for generating a time-varying magnetic field at the position of the implant device, whereby preferably said magnetic field generator comprises orientation means for changing the orientation of the magnetic field generated by said generator. "Changing the orientation of the magnetic field" hereby refers to a change in the polarization of the time-varying magnetic field and/or direction of propagation of accompanying electromagnetic waves. By using the orientation means, the generator can be arranged to provide a magnetic field which varies in time maximally along a longitudinal axis of the pickup coil, thereby efficiently inducing a current in said pickup coil. The orientation means may comprise a movable and/or rotatable arm or antenna-like structure, such as a U-shaped electromagnet. Preferably, said system comprises two implants such as disclosed here above.

In a similar aspect, the present invention provides a system for treating arterial hypertension by blocking renal sympathetic nerve signals via ablation by heating, comprising an implant as disclosed in this document, comprising a temperature-dependent LC-circuit, whereby said LC circuit comprises a resonant frequency which is temperature-dependent; a magnetic field generator for generating a time-varying magnetic field at the position of the implant device; a temperature measurement apparatus arranged for measuring said resonant frequency of said LC circuit and arranged for relating a measured resonant frequency to an implant temperature; temperature controlling means arranged for:
receiving said implant temperature from said temperature measurement apparatus;
comparing said implant temperature to a pre-determined ablation temperature;
controlling the time-varying magnetic field generated by said magnetic field generator on the basis of said comparison.

Preferably, said system comprises two implants such as disclosed here above.

In a further aspect, the present invention provides a method for the treatment of a patient with arterial hypertension by blocking renal sympathetic nerve signals via ablation of a substantially complete circumferential band or a spiraling band on one or more renal arteries' inner walls, comprising the steps of
implanting one or more implant devices in one or more renal arteries by means of a sheath and a guidewire, said implant devices each comprising an ablation region along at least a portion of their length, said ablation regions being adapted for surface contact with said renal arteries and said ablation regions subtending at least a substantially complete circumferential band or a spiraling band and being effective to ablate a signal-blocking path within said renal arteries upon application of energy to said implant devices;
retracting the sheath and guidewire;
subsequently heating the ablation region of the one or more implant devices by external energy-providing means, which are spatially separated from the implant device.

In a related aspect, the present invention provides a method for treating arterial hypertension by blocking renal sympathetic nerve signals via ablation by heating, comprising the steps of:
implanting one or more implants as disclosed in the present document, preferably comprising a pickup coil, a heater coil and a temperature-controlled switch or preferably comprising a temperature-dependent LC-circuit, whereby said LC circuit comprises a resonant frequency which is temperature-dependent, in one or more renal arteries;
applying a time-varying magnetic field at the position of said implants, thereby heating up said one or more implants to a pre-determined ablation temperature.

It should be stressed that in the above method, the heating of the implant device occurs after the surgical procedure. This improves the ease of the heating procedure and the comfort of the patient.

In a similar aspect, the present invention provides a method for heating one, two or more implant devices, which are suitable to be implanted in one, two or more vessels, comprising the steps of:
subsequently positioning said implant devices in said vessels by means of a sheath and a guidewire, said implant devices each comprising an ablation region along at least a portion of their length, said ablation region subtending at least a substantially complete circumferential band or a substantially spiraling band, said implant devices effective for ablating a signal-blocking path within said vessels upon application of energy to said implant devices;
retracting the sheath and guidewire;
heating the ablation region of said implant devices by external energy-providing means which are spatially separated from said implant devices
characterized in that said heating occurs after said sheath and guidewire are retracted and said heating of said implant devices occurs simultaneously.

In a preferred embodiment of the method, a recovery period is observed prior to heating the ablation region of the one or more implant devices by external energy-providing means. Furthermore, this recovery period is long enough to allow the one or more implant devices to be overgrown by bodily tissue. This recovery period may also be long enough to test if the implant devices are well positioned and do not move substantially within the vessel.

The advantages of observing a waiting period are multiple: the patient has time to recover from the surgical procedure, extra tests can be performed during the waiting period to check whether the implant device was well implanted, bodily tissue can overgrow the implant device, thereby improving the contact of implant device with the vessel's inner wall and thus improving the efficiency of the ablation procedure, etc.

In a particular preferred embodiment of the method, the step of heating the ablation region of the one or more implant devices by external energy-providing means, which are spatially separated from the implant device, is performed repeatedly at well-spaced time-intervals.

The presented method has the main advantage that in case multiple ablation procedures are necessary, no second surgical procedure is needed, i.e. the implanted implant device or devices can be reused for a second, third, . . . ablation procedure.

In a more preferred embodiment of the method, one or more implant devices as described in this document are being used. Thereby the implant devices can be engineered in order to produce the required effects by engineering their shape, size, material composition, magnetic and thermal properties, etc.

In a still more preferred embodiment of the method, use is made of a system as described in this document. In this case, the implant device can be heated by the external energy-providing means and a highly-controlled temperature of the ablation region of implant can be reached.

In a preferred embodiment, at least one implant device comprises a shape which is adapted for a renal artery.

In a preferred embodiment, said vessels comprise one or more renal arteries and said ablation regions of said implant devices being adapted for surface contact with said renal arteries and subtending at least a substantially spiraling band for ablating a signal-blocking path within said renal arteries upon application of energy to said implant devices.

In an embodiment of the method, the patient's vessels into which an implant is to be implanted are scanned using a 3D scanning technique such as CT or MRI to collect data on the varying diameter of the vessel e.g. when going from a distal to a proximal end of the vessel. From these data, one can derive the necessary shape and dimensions of the implants e.g. for all two renal arteries of a patient. This measuring can be done without a surgical procedure, thereby increasing the patient's comfort and wellbeing and reducing medical risks. After this measuring, the implants can be custom-made to fit the patient's vessel or vessels. Obviously, custom-made implants, in contrast with standard-sized implants, increase the success rate of any medical procedure.

The invention is further described by the following non-limiting examples which further illustrate the invention, and are not intended to, nor should they be interpreted to, limit the scope of the invention.

EXAMPLES

FIG. 1 represents a preferred embodiment of an implant 1 according to the present invention with circular cross-section (FIG. 1B) and elliptic cross-section (FIG. 1C). It should be clear that in the other figures showing embodiments of implants, the cross-sections can also be circular or elliptical, or basically any other shape which fits the vessel into which it is to be implanted best.

The represented implant 1 comprises a body 2, in this case shaped as narrowing tubular cage and made of metal wires 3 or the like, suitable to be placed inside a renal artery.

More in particular, the body 2 is provided of in this case three circular wires, a first bigger circular wire 4, an intermediate mid-sized second circular wire 5, and a third smaller circular wire 6.

The outlook of the body 2 may though be provided of more or less than three rings, for example two to five, more specifically three to four, or even more than five rings.

The first bigger circular wire 4 is connected with the intermediate mid-sized second circular wire 5 by means of in this case three straight inclined but upstanding wire portions 7.

In a similar manner, the intermediate mid-sized second circular wire 5 is connected with the third smaller circular wire 6 by means of in this case also three straight inclined but upstanding wire portions 8.

The wire portions 8 are here located at intermediate positions with respect to the wire portions 7.

The result is a narrowing tubular cage, which could also be described as a mainly conical or funnel shaped body 2, provided of three circular wires positioned at a distance from each other, at least when the body 2 is in a released or not compressed position.

In general terms, the self-expanding body 2 is preferably provided of a shape that fits the anatomy of the vein, for example a renal artery.

The circular wires may, according to a preferential embodiment, be provided of a mainly oval shape such that the body 2 is built up of different oval rings of converging diameter, preferably adapted to the anatomy of the renal arteries.

These rings of the body 2 will typically range in diameter from 3 to 30 mm, more specifically between 5 mm and 20 mm, even more specifically between 9 mm and 13 mm.

These rings of the body 2 will typically range from 5 mm to 50 mm, more specifically from 8 mm to 40 mm, even more specifically between 10 mm and 30 mm.

The body 2 has self-expanding properties thanks to the elastic characteristics of the material used, and thanks to the geometry of the body 2.

If a metal is used, it may be nitinol-based known for its superior self-expansion properties.

The self-expanding body 2 is conceived to stop expanding when it encounters a pressure of about 1 to 150 mm Hg, more specifically 3 to 80 mm Hg, more specifically 5 to 60 mm Hg, more specifically 10 to 40 mm Hg, equal to the distension pressure needed to alter the renal artery's anatomy.

Alternatively, a self-expanding cage may be conceived existing of different circular or oval shape rings that are interconnected. The rings may be formed so that a spiral form is created. The different rings of the spiral will also be interconnected so that upon heating or upon release of substances from the cage, no openings for recurrence of electrical signals are left open.

In this case, the material used is of the type that reacts, for example heats, in response to a remote applied alternating magnetic field.

The principle of hysteresis causes the metal of the cage to heat up, depending on the absorptive properties of the metal alloy that builds up the body 2.

Alternative is an electromagnetic field generator that changes polarity and therefore induces hysteresis heating in materials put inside the field. The system may use the Curie temperatures (the temperature to which a certain material can be heated, upon which further energy delivery does no longer change the temperature) that certain materials possess, as to the target temperature that should and can be reached. For example, $ZnFe_2O_4$ is a material that has a Curie temperature between 30 and 45 degrees Celsius.

A metal alloy cage that comprises $ZnFe_2O_4$ in its structure may therefore be heated to exactly 45 degrees, close to the target temperature desirable for appropriate ablation purposes.

Another alternative to deliver energy to the cage could be direct induction, using a magnetic core, again making use of hysteresis heating but in a more directive way.

Another alternative to deliver energy to the cage could be to use electromagnetic radiation through a thermical chemical-release system with external trigger, where the chemical is only released on demand and at the appropriate sites.

It is clear that still alternative energy field can be applied, such as electromagnetic radiation, hysteresis heating, reaching Curie temperature, direct induction, thermal/chemical release system, mechanical/chemical release system, indirect induction, Joule heating, acoustic energy, mechanical vibration, chemical release system.

Alternatively, the body 2 can be provided of toxic substances that are only released upon introduction into the renal artery, for example after applying an external energy field, which toxic substances then produce a lesion of limited necrosis/neurotoxicity.

In FIG. 2, an alternative embodiment of the implant 1 according to the invention is represented.

The body is built up out of braided metal wires 9 that have multiple interconnections, crossings and layers. This iteration allows for numerous connections with the renal vascular or other wall.

Figure 3A:
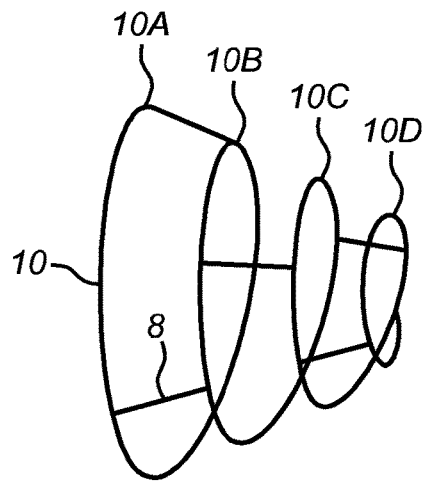
Figure 3B:
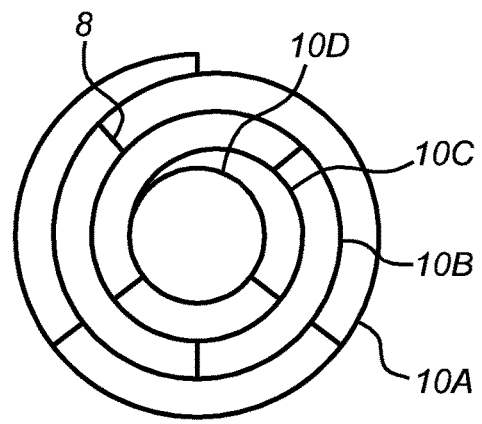

In FIG. 3, the implant 1 is conceived as a spirally shaped wire 10 of which the diameter gradually goes down along its longitudinal axis.

The windings 10A-10D, in this case four, are mutually connected with bridging upstanding wire portions 8.

This embodiment thus differs from the embodiment as represented in FIG. 1 by the single or continuous spirally shaped wire instead of the different circular wires 4-6.

The bridging upstanding wire portions 8, apart from giving structure and strength to the implant 1, also provide closed loops.

Indeed, the different windings 10A-10D are still interconnected to ensure, once the device is released, full and circular lesions in the renal artery.

Figure 4A:
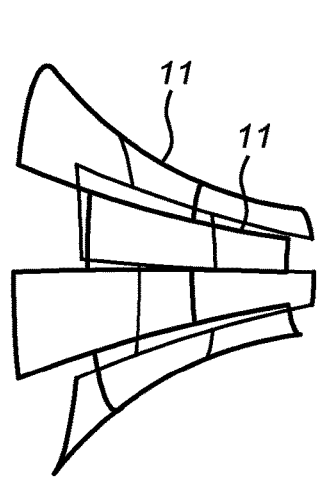
Figure 4B:
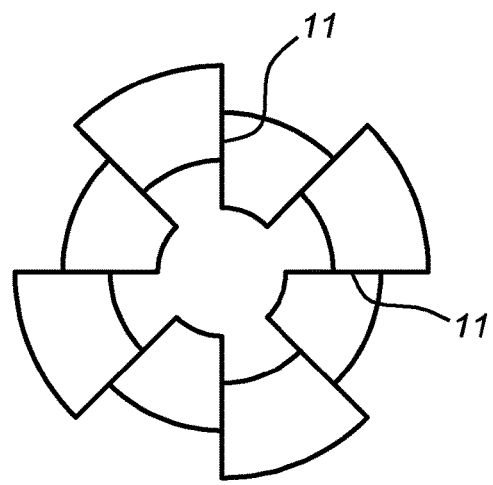

In FIG. 4 the implant shows longitudinal metal beads 11 that are outward bending, and that still show several interconnections between them, to ultimately form a metal cage.

An implant 1 according to the present invention may comprise portions made of different metal alloys with optionally different ferromagnetic properties and/or absorption coefficients, with specific response to alternating magnetic fields.

Alternatively, the basic structure of the implant 1 may be made of one and the same material, which may be provided of coating portions with varying properties.

Figure 5:
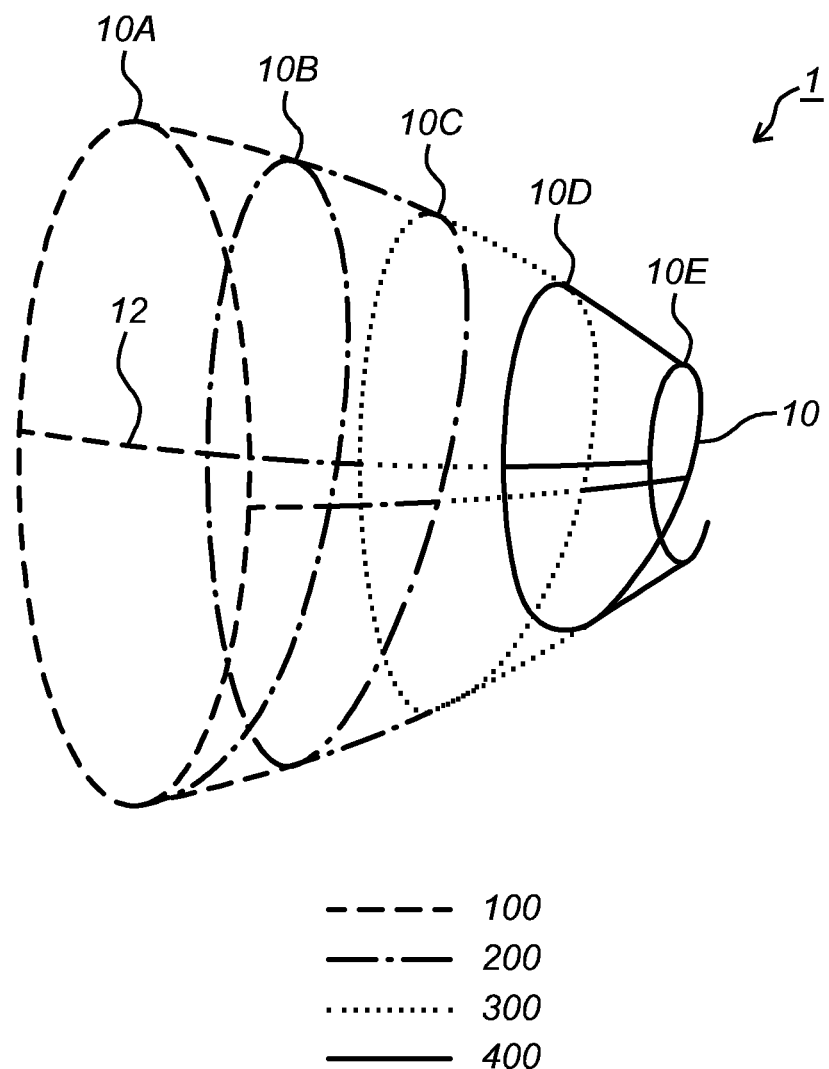

The embodiment illustrated in FIG. 5 shows an implant conceived as a spirally shaped wire 10 of which the diameter gradually goes down along its longitudinal axis, but where, as opposed to the embodiment represented in FIG. 3, the windings 10A-10E, in this case five, are mutually connected by means of bridging upstanding wires 12 which reach from the biggest winding 10A up till the smallest winding 10E.

The biggest winding 10A of the implant 1 is built up of a metallic alloy with self-expanding properties, and covered with a layer of a metal that has minimal ferromagnetic properties 100.

The next winding 10B is built up of the same self-expanding alloy, covered with a layer of material that has a higher rate of absorption of energy during the hysteresis phenomenon, and thus with altering magnetic fields will reveal different thermal heating properties 200.

The windings 10D and 10E most distal from the biggest winding 10A, to be located in a portion of the renal artery, is provided of a layer of material that has still a higher rate of absorption of energy during the hysteresis phenomenon 400.

Figure 6:
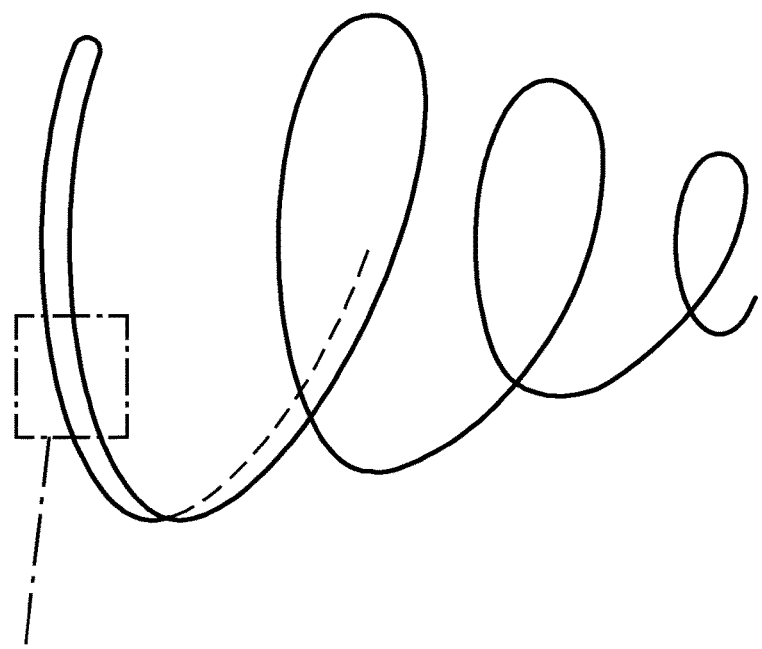
FIGS. 6 to 8 schematically represent a detail of a portion of an implant according to the invention.
Figure 6:
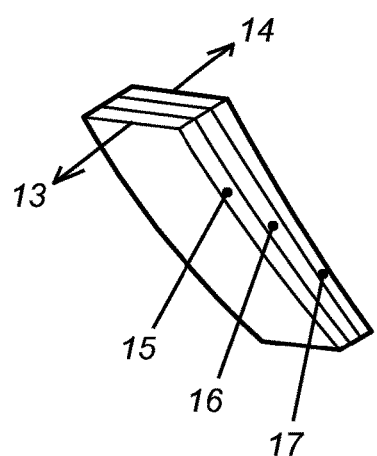

According to another embodiment of the implant 1, a portion of which is schematically represented in FIG. 6, the wire building up the body 2 of the implant 1 is composed of different layers, in this case three layers made of different alloys 15, 16 and 17.

These different alloys are in contact with each other, and depending on different magnetic fields to be applied, they will exhibit different properties.

It is clear that alternatively or in combination with the above or other features, one or more layers can have high thermal isolation characteristics, in order to direct heat where needed, and to isolate portions to prevent undesired heating of blood or tissue.

Figure 7:
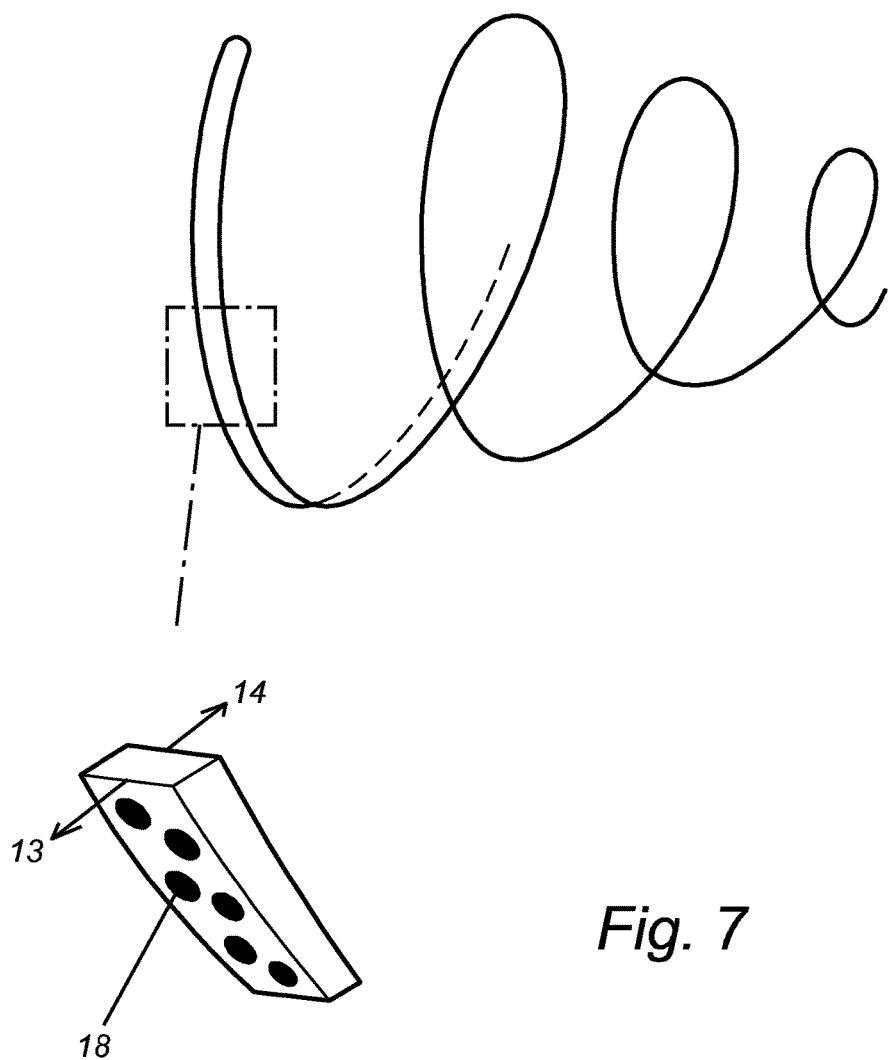

According to another embodiment of the implant 1, a portion of which is schematically represented in FIG. 7, the body 2 is provided of micropores 18 at the abluminal side 13 (in contrast with the adluminal side 14) wherein substances are provided.

Such substances may for example be a selection or a composition of one or more of the following substances:
 ethanol;
 tetrodotoxin and batrachotoxin;
 maurotoxin, agitoxin, charybdotoxin, margatoxin, slotoxin, scyllatoxin or hefutoxin;
 calciseptine, taicatoxin, calcicludine, or PhTx3;
 botulinum toxide;
 cytochalasin D, rapamycin, sirolimus, zotarolimus, everolimus, paclitaxel;
 glutamate;
 isoquinoline;
 N-methyl-(R)-salsolinol;
 Beta-carboline derivates.

The micropores 18 are closed when the body is coiled together, for example prior to the provision in a guiding catheter system, and upon release into its site of destination, upon expansion, these micropores 18 open so that the substances inside the metal arms of the cage can be released.

Figure 8:
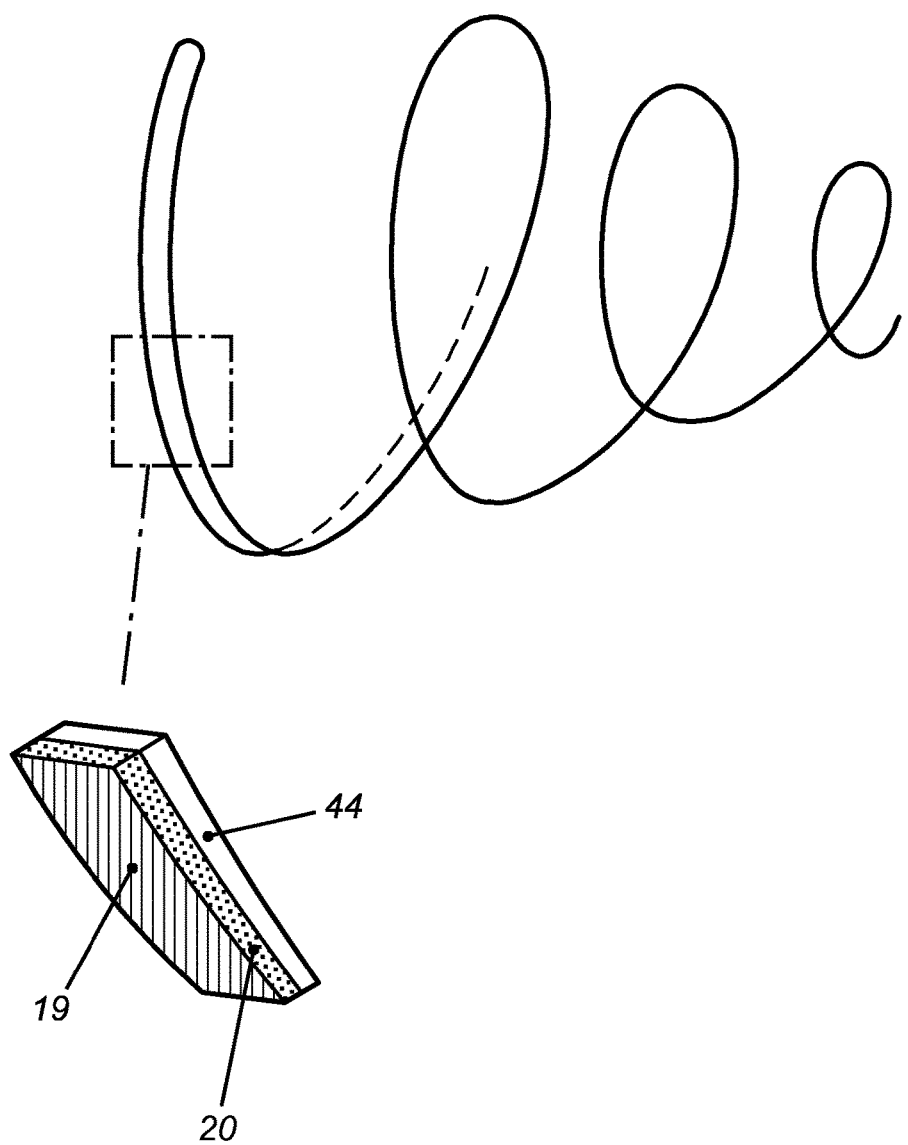

According to another embodiment of the implant 1, a portion of which is schematically represented in FIG. 8, the body 2 is covered by a thermoactive coating 19 which is only activated upon temperatures above 35° C. so that the body temperature would trigger activation.

Alternatively, a thermoactive coating 19 can be provided which is only activated upon temperatures above 45° C. so that an external application of an energy field would trigger activation.

Alternatively, an insulating material 44 can be provided at the parts of the implant which comes into contact with parts of the body which are preferably not heated such as some parts of the vessel wall or the blood. Hereby the parts of the implant which are heated are thermally insulated from e.g. the blood.

The energy field could for example be a remote applied alternating magnetic field, heating the body 2 of the implant 1 thanks to a hysteresis effect.

At the said activation temperature, the coating 19 gets absorbed, and the active component that is residing below the coating 20 is released into the vascular or arterial wall.

Note that the elongated shape and/or the expanding forces provide can be considered as anchoring means of the implant 1.

Figure 11:
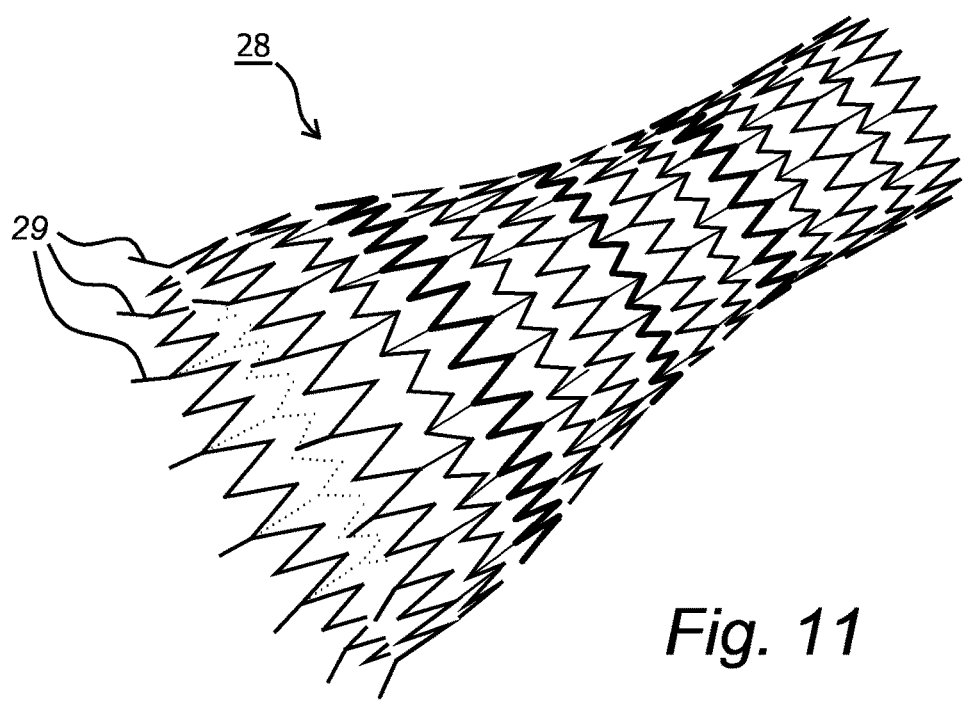

Alternatively, hooks or barbs or the like 29 can be provided as in FIG. 11 on the outwardly directed portions of the implant 1, providing guaranteed anchoring of the implant 1 once it put in place.

According to still another embodiment, the outer rings or other cage structures that are fitted into the vessel, or the whole cage may be equipped with structures to increase the solidity of cage immobility, to ascertain the fixed position of the implant, to reduce the possibility of movement of the implant after the implantation.

The method of placing the implant is easy and can be performed as hereafter described.

According to the known practices, a catheter 30 with guidewire 31 is introduced up till the place where the implant 1 is to be left. This is shown schematically in FIGS. 12 and 13.

Pull-back of the catheter while leaving the implant 1 in position causes the implant 1 to expand.

As the shape and/or elastic characteristics of the implant 1 is/are suitably adapted to fit and optionally press against the arterial or venous structure, for example in the renal artery, the implant 1 is left in a safe and self-anchoring manner.

After full pullback of the catheter, the implant 1 is fully released.

Alternatively, the well-known balloon expansion can be applied.

An appropriate period can be awaited prior to applying an external energy field in order to trigger the triggerable portions of the implant 1.

Various consecutive treatments by simply applying an appropriate energy field can be considered, without the need to perform renewed invasive surgery, which is the main advantage of the implant and the system according to the present invention.

Furthermore, in case where the implant 1 is provided of varying substructures, each with their own response to an externally applied energy field, varying treatments can be considered, for example with increasing intensity.

Each portion can for example be triggered with a remote applied alternating magnetic field characterized with a specific frequency.

It is clear that when reference is made to lesions, these may concern transmural lesions extending up till the exterior wall, and that lesions may be continuous, as opposed to discrete or composed partial lesions.

The present invention is by no means limited to the embodiments described by way of example and represented in the accompanying drawings; on the contrary, such an implant and system of an implant and excitation device for the treatment of arterial and venous structures according to the invention can be made in all sorts of shapes and dimensions while still remaining within the scope of the invention.

Figure 9:
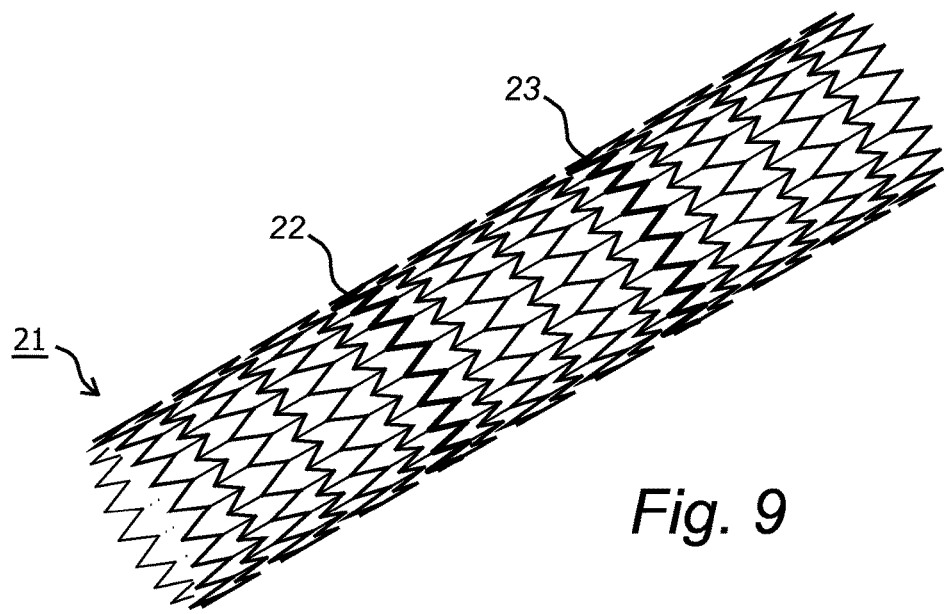

FIG. 9 shows a circular braided implant 21 in which one circumferential region 22 comprises an alloy with a specific Curie temperature and in which a second circumferential region 23 comprises an alloy with another specific Curie temperature.

Figure 10:
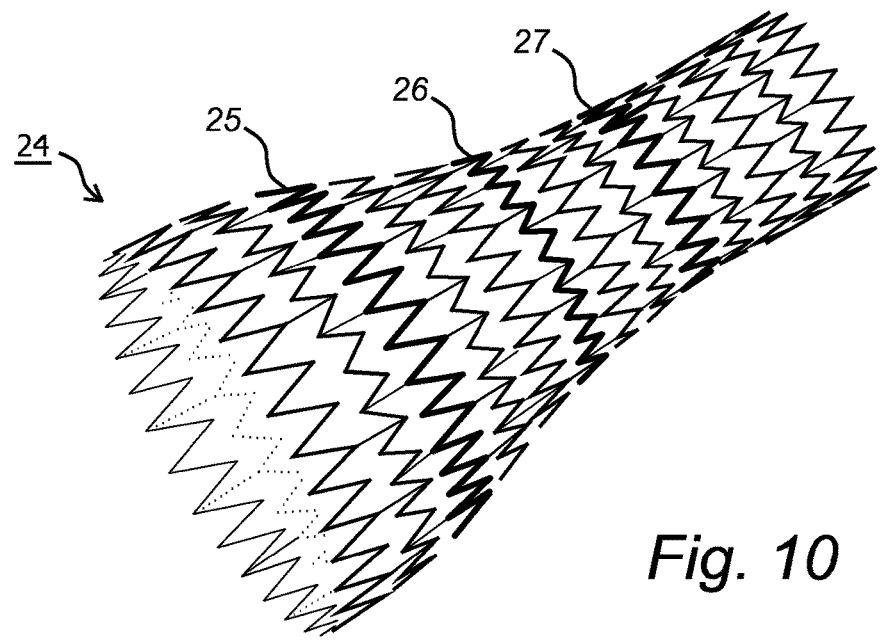

FIG. 10 shows a funnel-shaped braided implant 24 in which one circumferential region 25 comprises an alloy with a specific Curie temperature, in which a second circumferential region 26 comprises an alloy with another specific Curie temperature, and in which a third circumferential region 27 comprises an alloy with still another specific Curie temperature.

FIG. 11 shows a funnel-shaped braided implant 28 with anchoring means 29 in the form of small barbs.

Figure 13:
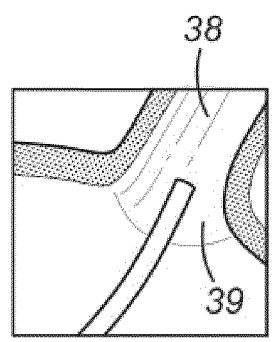
FIG. 13 schematically shows the way the catheterization can be done in order to deliver one or more implants to a vessel.

FIG. 13 shows how a catheter tip can be guided, e.g. through an insertion vein or artery, to e.g. a renal artery 38.

Figure 14:
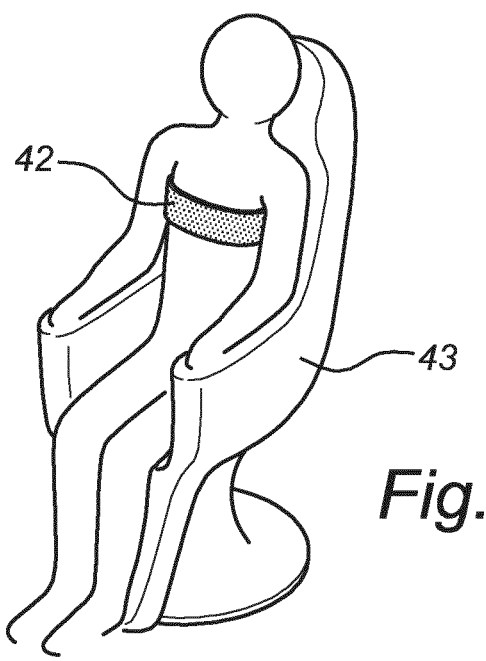
FIG. 14 schematically represents an embodiment of the external energy-providing means as it can be used for treating a patient.

FIG. 14 represents an embodiment of the external energy-providing means 42 as it can be used for treating a patient during the ablation procedure 43.

Figure 15:
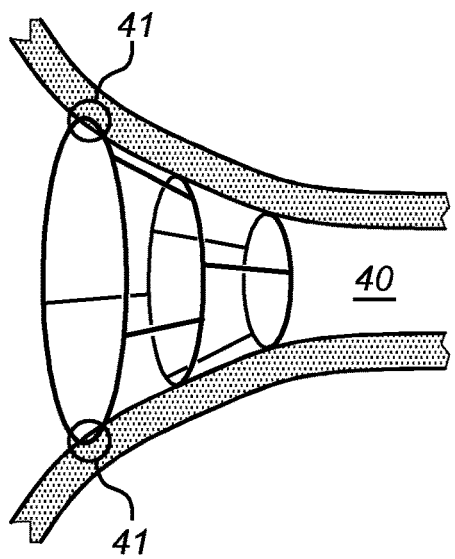
FIG. 15 schematically represents an embodiment of an implant in place in the vessel.

FIG. 15 shows an implant in place 40 and the ablation region in cross section 41 in a conical section of a vessel.

Figure 18:
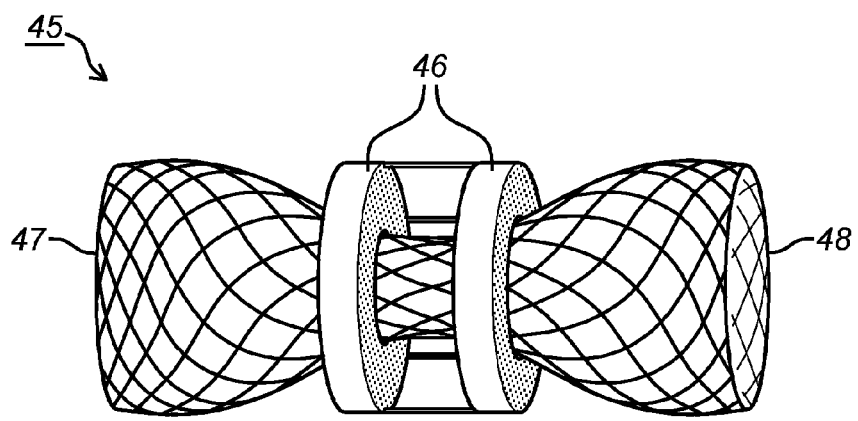
FIG. 18 shows an embodiment of an implant which has an hour-glass shape, whereby near the middle region, where the diameter becomes smaller, a set of heating rings is attached around the hour-glass shaped part of the implant.

FIG. 18 shows another embodiment of an implant which has an hour-glass shape 45, whereby near the middle region, where the diameter becomes smaller, a set of heating rings 46 is attached around the hour-glass shaped part of the implant. The heating rings are attached to the hour-glass shaped part in a thermally insulating manner such that little heat is transferred to the blood stream when the heating rings are heated. Furthermore the heating rings are meant to be completely separated from this blood stream, since the hour-glass shaped part may be covered by a blood-tight tissue and may be clamped into the vessel at or near the implant ends 47 and 48.

FIG. 19 shows an embodiment of an implant comprising a fuse, so that at certain temperatures, more specific the temperature that is reached to achieve an optimal ablation, between 40 and 80 degrees Celsius, more specifically between 45 and 60 degrees Celsius, the circuit that may be generated gets interrupted. This comes from the phenomenon that when an implant, more specifically a metallic implant, more specifically a nitinol implant is brought into the alternating magnetic field, an electrical current is generated through the metal implant itself, thus generating accelerated heating by itself (induction and Joule heating). This phenomenon results in extremely rapid heating of the implant, that can be stopped by interrupting the electrical current that may run through the implant. This stopping of the current may be caused by a fuse that is mounted within the metallic implant, and that for instance may exist of a resistance, that breaks when it is heated above a certain temperature. In this case, the fuse would stop heating up further above a temperature of 45-60 degrees, more specifically 50-55 degrees. FIG. 19a shows a detailed view of the fuse.

In a different configuration, as shown in FIG. 20, the metal implant can be build up of memory shape alloys, so that upon heating of the device, the different metallic parts take up another configuration, thereby interrupting the electrical current that can run through the implant. Details of the on and off position of the switch or fuse are shown in FIGS. 20a and 20b respectively. This different, i.e. open, configuration consists potentially of the original form of the metal, so that it goes back to its "memory shape". This is called a "shape memory metal".

In a still different configuration as shown in FIG. 21 and a detail in FIG. 21a, the implant consists of two different materials, where upon heating the bondage between the two different metals gets interrupted, so to stop the electrical current from running through the implant.

Another addition of this application is that the heating needs to be unidirectional. The blood needs to be isolated from the heating because of two reasons: first, blood should not be heated because proteins in the blood can denature and form clots, and second, because blood is a huge heat dissipator that may subtract too much heat away from the implant, it would need too much energy to get the ablation region of the implant to the desired temperature. Therefore, an extensive coating is formed around the implant, but almost exclusively on the ADLUMINAL side as illustrated in FIG. 22, so that when the implant is heated, no heat is dissipated towards the blood stream.

FIG. 23 illustrates the concept of the present invention whereby an implant device (55) is provided with a built-in thermal switch (54). Hereby, said implant may be activated by applying a time-varying magnetic field $\phi$, e.g. a radiofrequent field as can be produced by an electromagnet or electromagnetic coil or antenna (51). Said time-varying magnetic field $\phi$ may induce a current in said electrical circuit, through said pick-up coil (53) and said heating coil (52), if said switch (54) is closed. Whether the switch is closed or open, depends on the temperature at the position of the switch or at a position of a temperature sensor attached to said switch, preferably via a thermostat.

FIG. 24 illustrates the dimensions of an implant in an expanded position in a vessel. Hereby, the vessel (65) is typically between 5 mm and 50 mm wide, e.g. 20 mm in diameter. The heater coil (62) can be about 20 mm long, while the pickup coil (63) can be, and preferably is, longer than 20 mm. The thermal switch (64) in FIG. 24 is positioned near the heater coil (62) and is open or closed depending on the temperature at or near said heater coil. The heater coil subtends a circumferential ablation region of the vessel over the heater coil length.

Figure 25A:
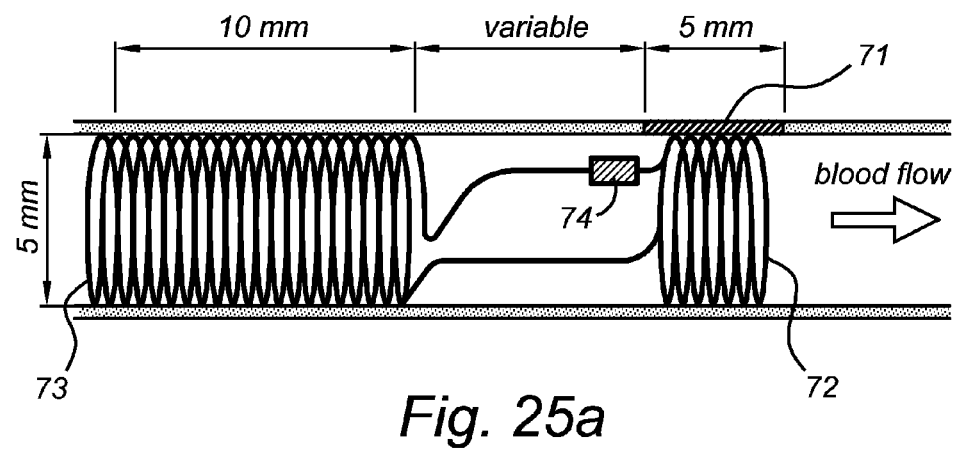
Figure 25B:
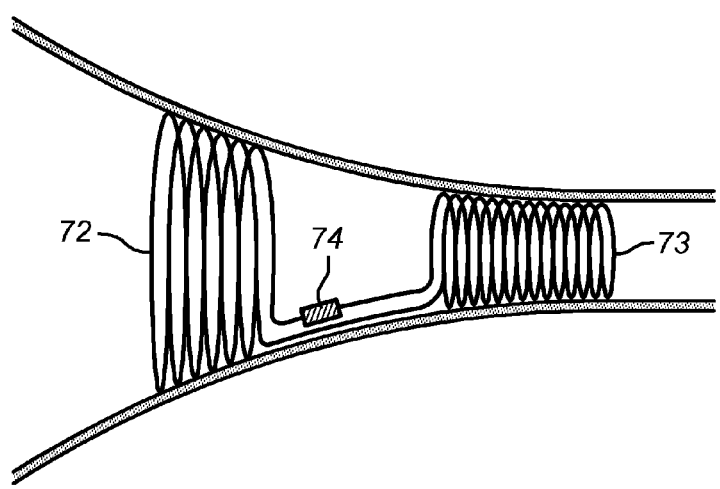
Figure 25C:
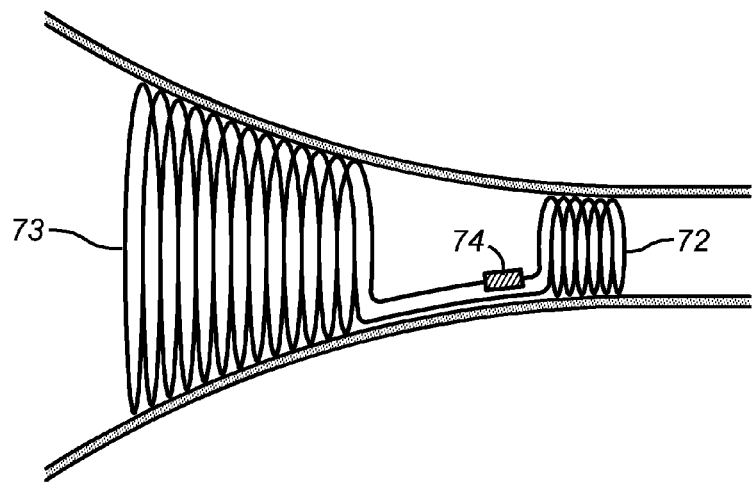
Figure 25D:
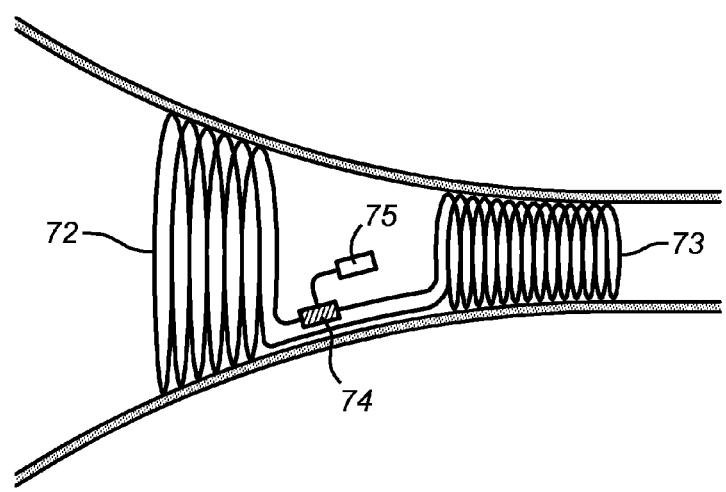
Figure 25E:
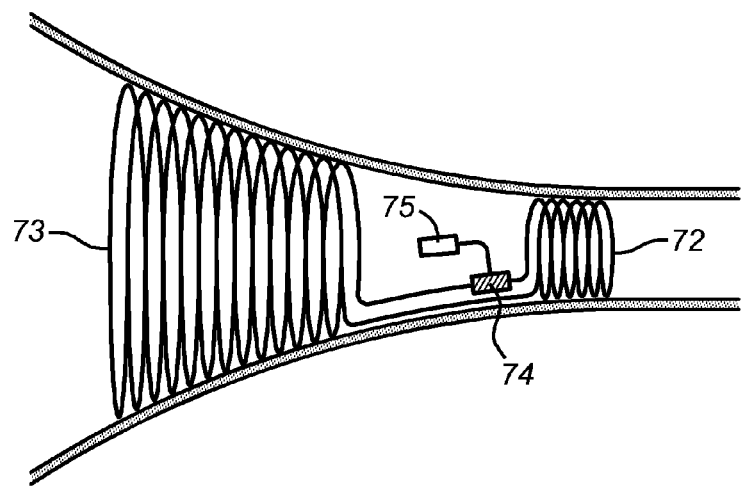
Figure 25F:
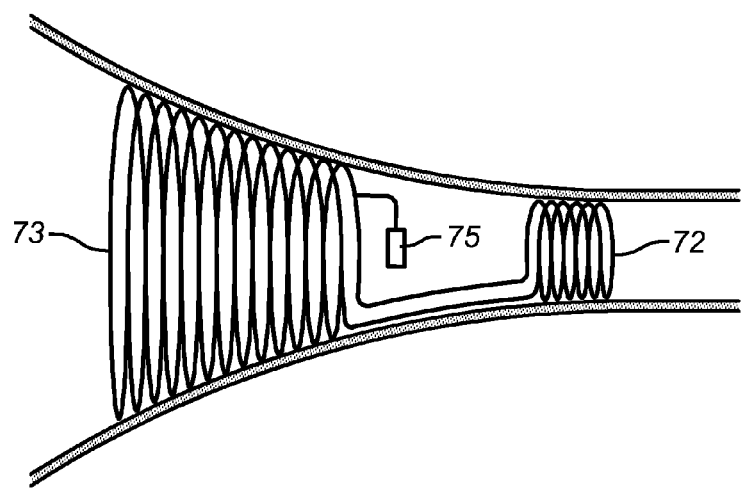
Figure 25G:
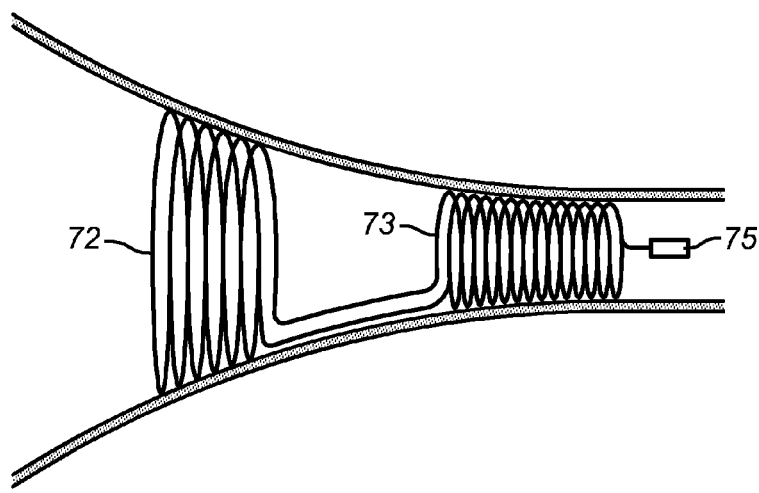

FIGS. 25a-g illustrate different embodiments of the present invention, whereby the shape and absolute and relevant sizes of the coils may differ between different embodiments. A heater coil (72) and a pickup coil (73) can be clearly identified, the pickup coils (73) as presented comprising a large amount of windings to increase their inductances. A thermal switch (74), in FIGS. 25a-e attached to a printed circuit board and coated, is coupled to heater coil (72) and pickup coil (73). In FIGS. 25d-g, a pcb (75) comprising one or more electronic circuitry, possibly including a thermal switch and/or a supply circuit coil is coupled to the pickup coil (FIG. 25f-g) or switch (FIG. 25d-e). The shape of the coils can be arranged to fit into a specific vessel, e.g. a cylindrical vein or artery (FIG. 25a) or a cone-shaped vein or artery (FIG. 25b-g). In particular for renal arteries, a cylindrical-shaped heater coil for implantation in the lumen of the artery is preferred.

A winding of the heater coil (76) induces a temperature profile (77) in the wall (78) of the vessel upon activation of the implant. This is illustrated in FIG. 26, where it is illustrated that the heat is deposited mainly near the winding, but that it is possible that also the outer side of the vessel (79) can be heated to an increased temperature. Appropriate modelling of the vessel and testing of the setup allows to set the optimal temperature for the implant to ablate a signal-blocking path on the inner wall of the vessel, without unnecessary damaging tissue which should remain intact.

Further embodiments comprising e.g. a PTC (80) or thermistor switch, are illustrated in FIGS. 27a-b for essentially cylindrical implants.

In some embodiments, it is necessary or advisable to use electrical components which need DC current or voltage to operate. In such embodiments, it is necessary that the implant comprises an AC-DC converter in order to convert AC current flowing via induction in at least part of the circuitry of the implant, to DC current.

This converter may obtain an AC input current from the pickup coil or from a supply circuit coil. Such a converter may be part of a larger electronic circuit which can be attached to a pcb (81) and coupled to the coils as illustrated in FIG. 28.

FIGS. 29a-d illustrate electronic circuits which can be used in embodiments of the implant of the present invention. If a large current is sent through a heater wire or heater coil, the heater coil generates heat and the temperature around the heater coil rises. If there is no current through the heater coil, the temperature drops because of cooling inside a bloodstream. For ablation, a target temperature around 55° C. may need to be reached and held for an amount of time. A digital thermostat PCB (IC1) measures the temperature by means of a temperature sensor and switches the large current through the heater coil on or off by means of a switch (IC3), hereby forcing the temperature around the heater coil to rise or drop. The heater coil is powered by means of the energy induced in a large pickup coil. The control circuit is powered by a separate coil.

Figure 29A:
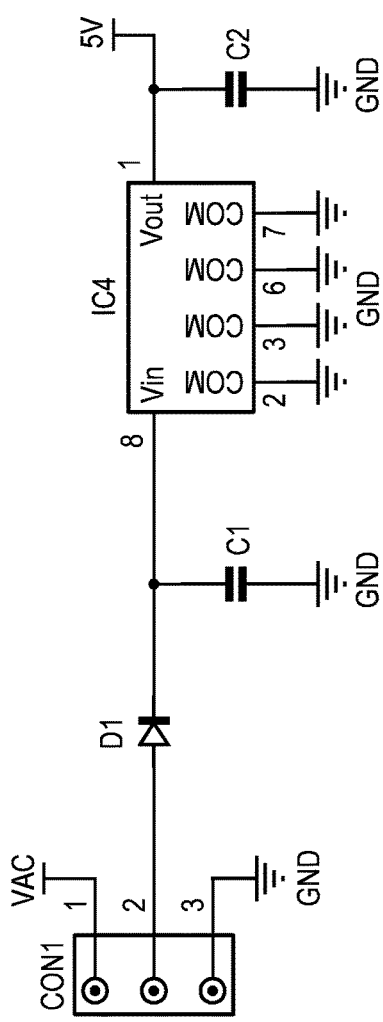
Figure 29B:
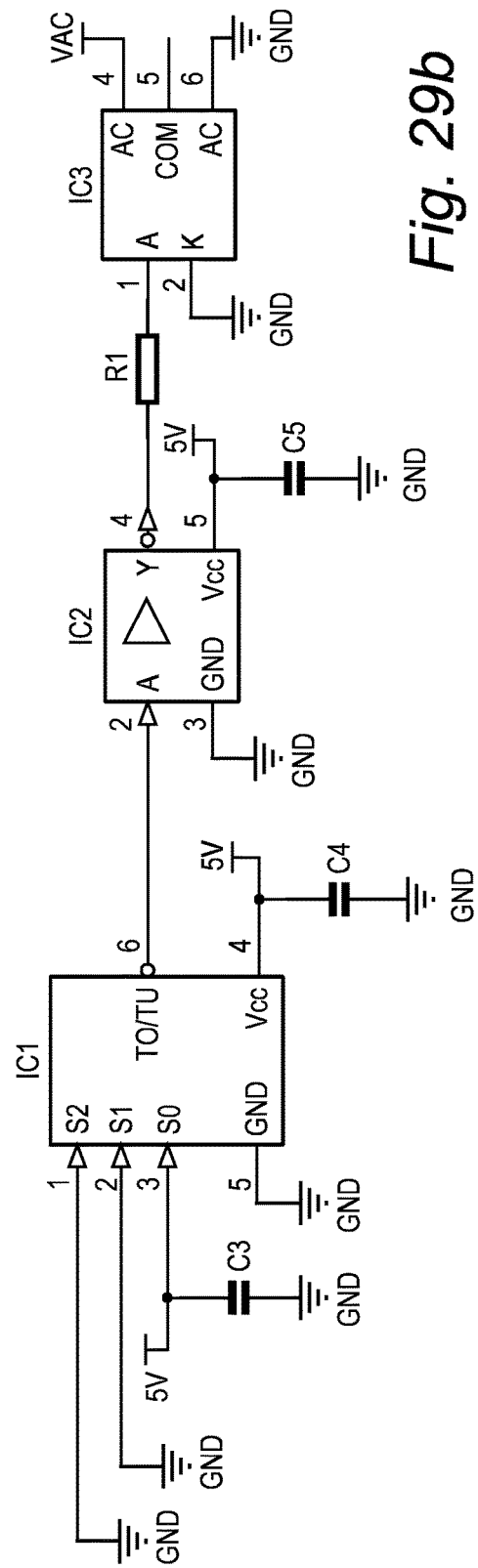

The temperature sensor measures the internal temperature and compares it to 55° C. with a hysteresis loop of 2° C. This chip provides a high output voltage level (5 V) if the measured temperature is higher than 55° C., and a low output voltage level (0 V) if the temperature is lower than the target temperature of 55° C. This thermostat chip (IC1) is used to control a switch (IC3), which in this case is a solid-state relay (SSR) with integrated optocoupler, as this SSR is able to switch the alternating current induced by the pickup coil. As this switch (IC3) requires a larger current than the temperature sensor can provide (the thermostat chip may have a very low output current driving capability), a buffer needs to be used. As a high switch input voltage results in a closed state and a low voltage results in an open state, this buffer is realised by means of an inverter (IC2) with large output current. A resistor (R1) of e.g. 330 Ohm between switch (IC3) and inverter (IC2) limits the switch drive current, hereby protecting the switch input. This chain (FIG. 29b) provides the temperature control. As this chain consists of active devices, this can only work if adequately supplied. The chain in FIG. 29a provides a stable 5 V supply voltage out of an input AC-voltage delivered by a separate circuit supply coil. This coil provides a lower AC-voltage than required for the power chain. The input AC-voltage is transformed into a DC-voltage by a half-wave rectifier (D1) higher than the target 5V. Then a 5V linear regulator (IC4) is used to transform this voltage into a stable 5 V power supply. The capacitors, e.g. of 100 nF, visible throughout the design are placed for decoupling (local stabilization of the supply voltage).

The symbols GND, VAC and 5V each represent a net, connecting the symbols with the same name. These have no physical meaning other than just another connection. GND is the universal sign for a voltage reference (as all voltages need to be referred to some point inside a circuit). This is not to be mistaken for an earth connection. GND is often chosen to be a connection with very low impedance, and therefore often realized as reference plane.

The connector CON1 is the interface for the heater coil (pin 1), the circuit supply coil (pin 2) and the voltage reference GND (pin 3).

Figure 29C:
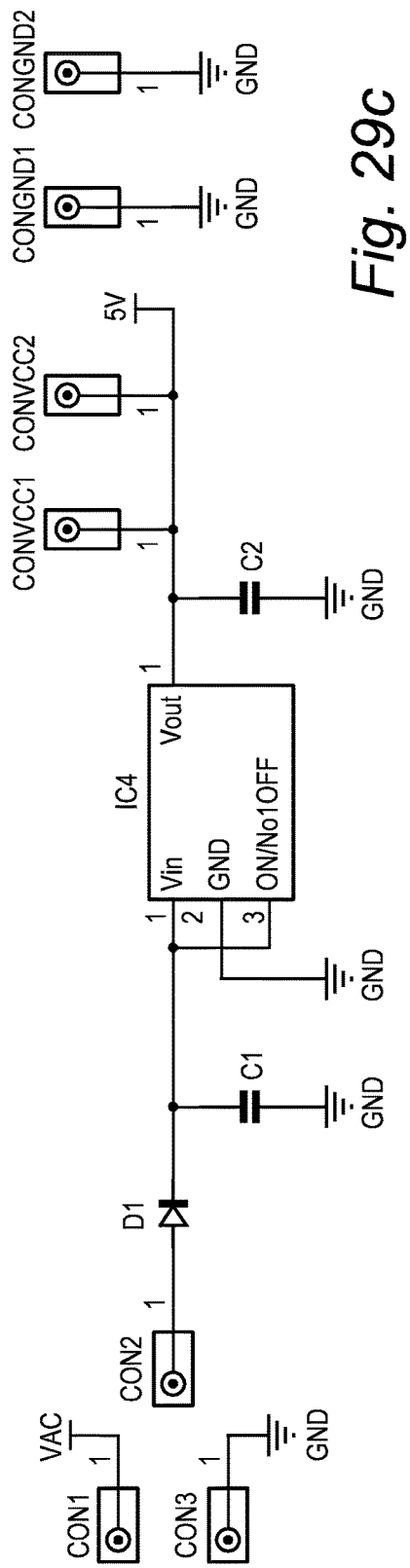
Figure 29D:
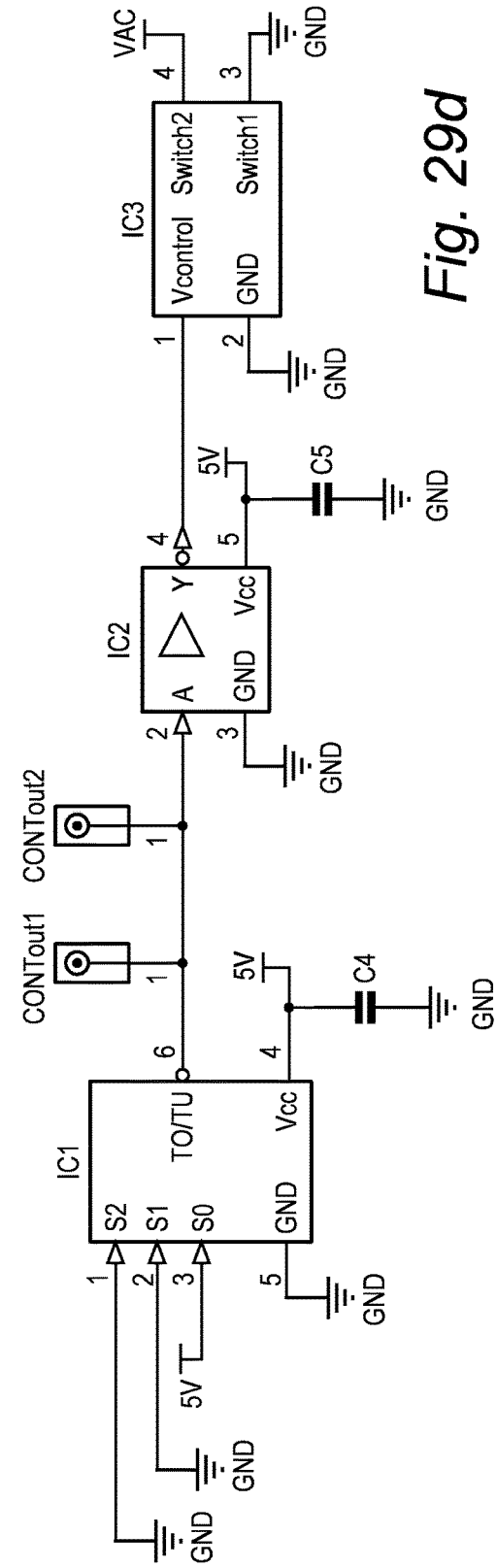

Another embodiment of the electrical circuitry is illustrated in FIGS. 29c-d. This board is a smaller version as the one presented in FIGS. 29a-b. The functionality remains identical, but it uses smaller components. The regulator (IC4) is different and the switch and resistor are combined into one component (IC3). Also the large connector is changed into three smaller connectors CON1-CON3. The extra connectors CONVCC, CONGND and CONTout can be used to split the board into a small board with a temperature sensor and another board with the remainder of the chips. This way, the small temperature sensor can be brought much closer to the heater coil.

Figure 29E:
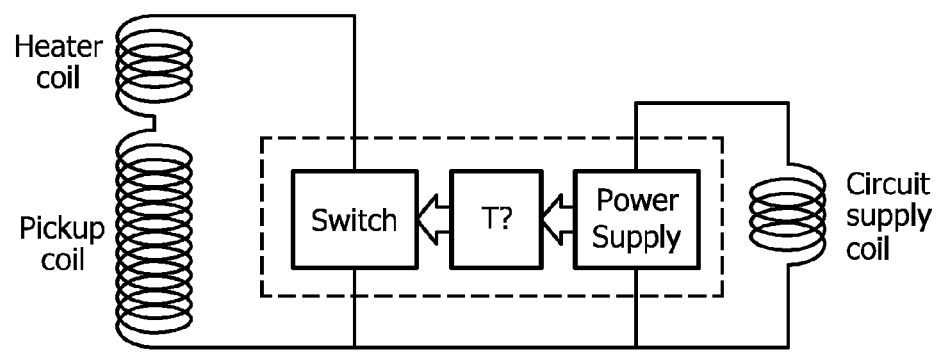
Figure 29F:
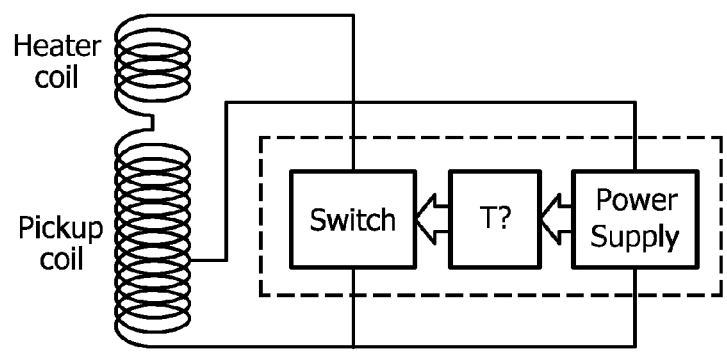

In FIGS. 29a-d, embodiments of an implant according to the present invention are illustrated, whereby the implants comprise a separate supply coil with a dedicated supply circuit for providing the other components such as the thermostat, inverter and switch with a constant DC voltage of e.g. 5V, as illustrated in FIG. 29e. In other embodiments of an implant according to the present invention, a center tap may be used at the pickup coil side to obtain the circuit power instead of a separate circuit power supply coil (FIG. 29f). This seems easier to integrate in an implant instead of using a third coil. This latter embodiment may pose the following extra problem: The center tap may be situated inside the switching chain. If a large current is flowing through the coil combination, this current generates a magnetic field counteracting the external magnetic field that actually caused this current to flow. This results in a voltage drop across the coil terminals. This means that in case of a closed switch, the voltage across the coil terminals can be much lower than in case of an open switch. This voltage difference could cause regulators to fail due to high power dissipation. To solve this problem, extra components need to be added to the circuit to prevent this. Such components may be added in e.g. a miniaturised chip design.

FIGS. 30a-34 illustrate embodiments of external energy providing means which can be used in a system or method of the present invention for providing energy to the implant by providing a time-varying magnetic field at the position of the implant.

Figure 30A:
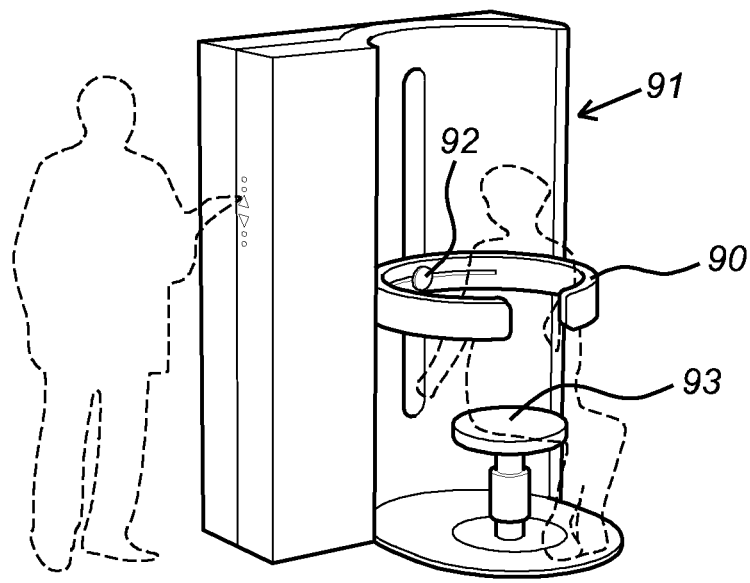
Figure 30B:
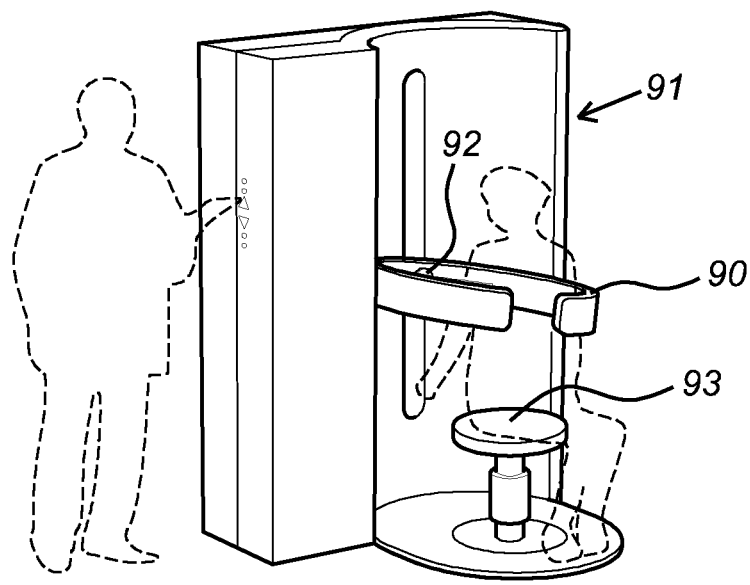
Figure 33:
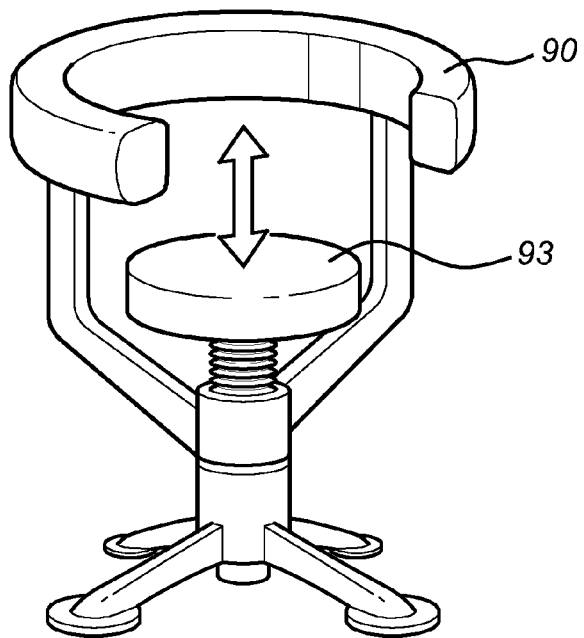
Figure 34:
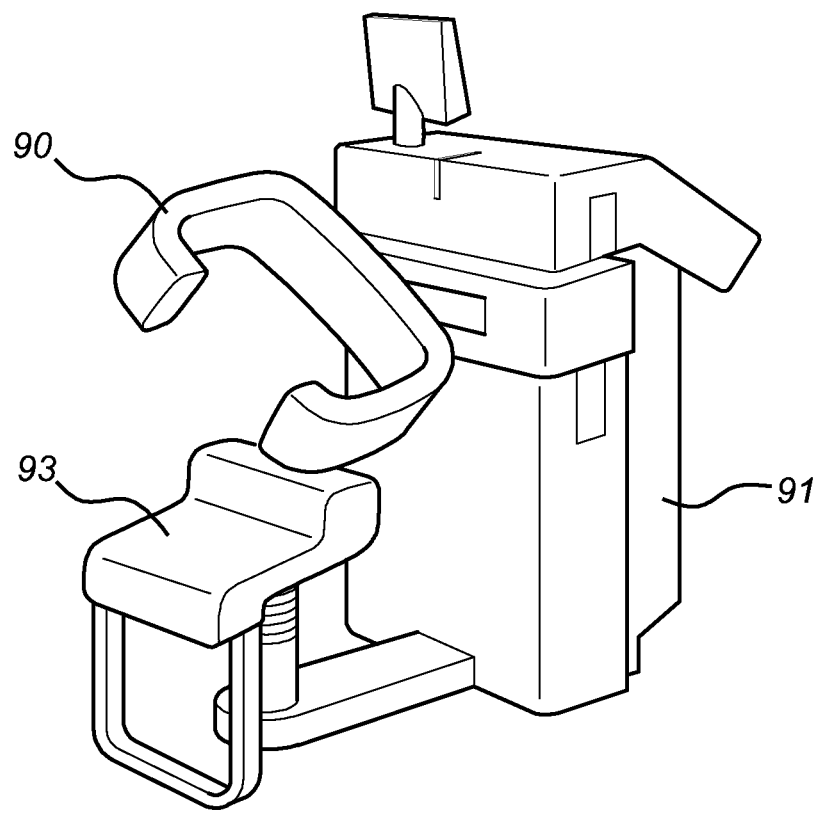

FIGS. 30a-b and also FIGS. 33-34 illustrate an embodiment whereby a patient with an implant may sit down during the heating procedure, as a time-varying magnetic field is produced preferentially within the arc-shaped arms (90) of the generator (91). The arms are capable of being rotated, preferably around a horizontal axis (92) and the patient chair (93) may also be rotated, preferably around a vertical axis, and may be moved up and down, such that an optimal induction coupling between magnetic field of the generator and induced field in the implant is reached. The optimal position of the generator may depend on the patient, and on the orientation of the treated vessels in the patient. Therefore a generator as illustrated in these figures, whereby both the orientation and magnitude of the magnetic field may be varied in time, is particularly preferred in the systems and methods presented in this document.

Figure 31:
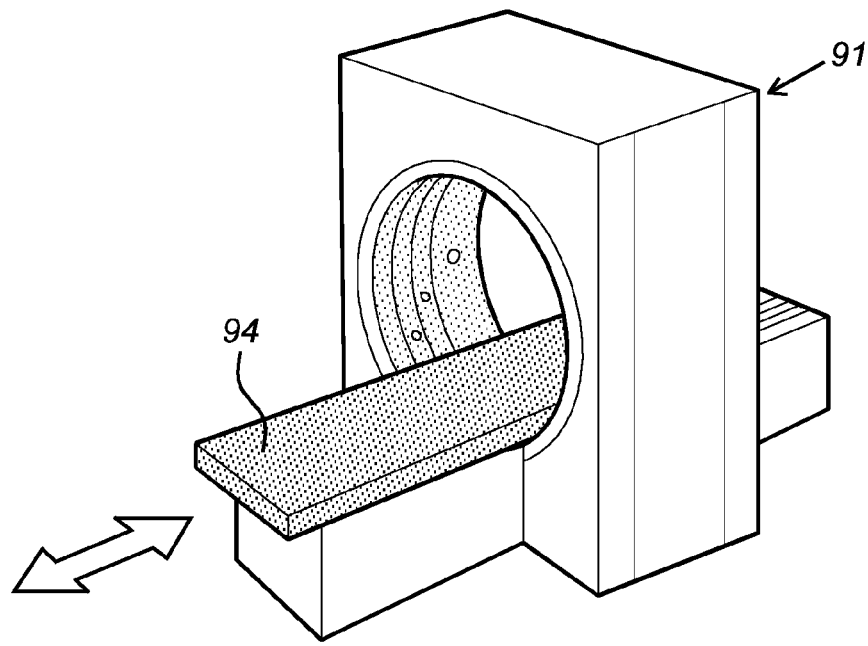

FIG. 31 illustrates the possibility of using a large magnetic field generator (91) around a table (94) onto which a patient can lie down for treatment. The table can move horizontally through the generator.

Figure 32A:
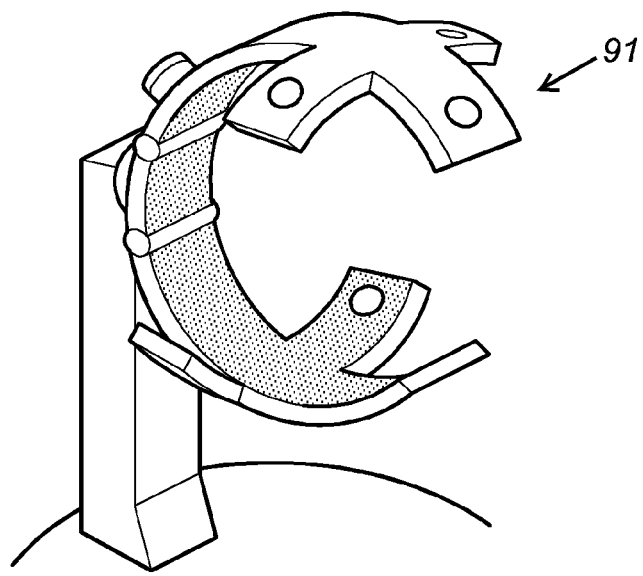
Figure 32B:
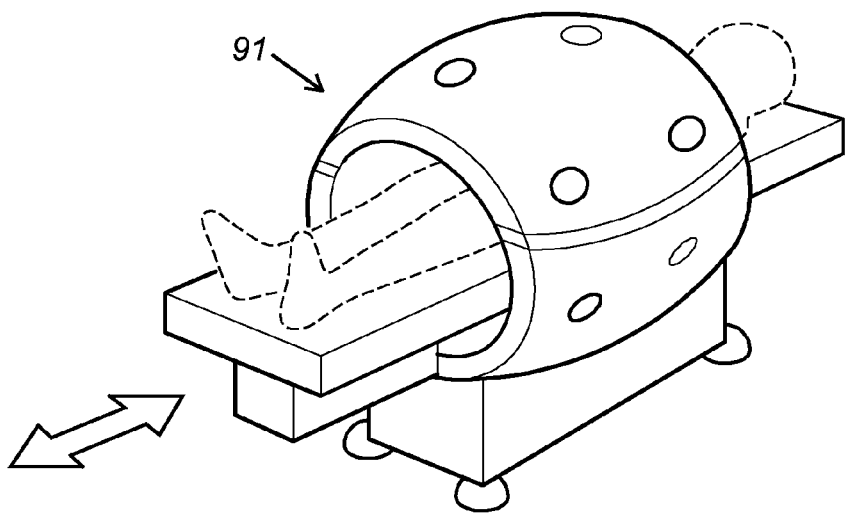

FIGS. 32a-b illustrate a magnetic field generator (91) which is capable of generating fields in different orientations, whereby the orientation which is optimal for inducing a current in the implant can be adapted in a patient-dependent manner.

It is supposed that the present invention is not restricted to any form of realization described previously and that some modifications can be added to the presented example of fabrication without reappraisal of the appended claims. For example, the present invention has been described referring to renal arteries, but it is clear that the invention can be applied to other vessels for instance.

The present invention concerns, but is not limited to:

1. Method for heating one, two or more implant devices which are suitable to be implanted in one, two or more vessels, comprising the steps of:
   subsequently positioning said implant devices in said vessels by means of a sheath and a guidewire, said implant devices each comprising an ablation region along at least a portion of their length, said ablation region subtending at least a substantially complete circumferential band or a substantially spiraling band, said implant devices effective for ablating a signal-blocking path within said vessels upon application of energy to said implant devices;
   retracting the sheath and guidewire;
   heating the ablation region of said implant devices by external energy-providing means which are spatially separated from said implant devices
   characterized in that said heating occurs after said sheath and guidewire are retracted and said heating of said implant devices occurs simultaneously.
2. Method according to point 1, whereby at least part of each of said implant devices is made from at least one material which shows magnetic hysteresis, such as a ferromagnetic, ferrimagnetic or anti-ferromagnetic material.
3. Method according to point 2, whereby said implant devices comprise a ferrous fluid.
4. Method according to any of the points 1 to 3, whereby heating occurs by external energy-providing means which create a time-varying magnetic field at the position of said implant devices.
5. Method according to any of the points 1 to 4, whereby at least one of said implant devices comprises a thermoactive coating comprising an activation temperature between 35° C. and 37° C. so that the body temperature would trigger activation.
6. Method according to any of the points 1 to 4, whereby at least one of said implant devices comprises a thermoactive coating comprising an activation temperature above 45° C. so that activation is triggered only when said ablation region is heated by said external energy-providing means.
7. Method according to any of the points 1 to 6, whereby said implant devices comprise substances capable of producing a lesion of limited necrosis and/or neurotoxicity.
8. Method according to point 6, whereby at least one of said implant devices comprises cavities which are filled with said substances and which open when the implant is heated.
9. Method according to any of the points 6 to 8, whereby at least two substances are mixed before being released, e.g. to deliver a two-component neurotoxine.
10. Method according to any of the points 6 to 9, whereby said substances are a selection or a composition of one or more of the following substances:
    ethanol;
    tetrodotoxin and batrachotoxin;
    maurotoxin, agitoxin, charybdotoxin, margatoxin, slotoxin, scyllatoxin or hefutoxin;
    calciseptine, taicatoxin, calcicludine, or PhTx3;
    botulinum toxide;
    cytochalasin D, rapamycin, sirolimus, zotarolimus, everolimus, paclitaxel;
    glutamate;
    isoquinoline;
    N-methyl-(R)-salsolinol;
    Beta-carboline derivates.
11. Method according to any of the points 1 to 10, whereby at least one implant device comprises a shape which is adapted for a renal artery.
12. Method according to any of the points 1 to 11, whereby said vessels comprise one or more renal arteries and said ablation regions of said implant devices being adapted for surface contact with said renal arteries and subtending at least a substantially spiraling band for ablating a signal-blocking path within said renal arteries upon application of energy to said implant devices.
13. Method according to any of the points 1 to 12, whereby a recovery period is observed prior to heating the ablation region of the one or more implant devices by external energy-providing means, whereby said recovery period is long enough to allow the implant devices to be incorporated into the vessel's wall.
14. Method according to any of the points 1 to 13, whereby the step of heating the ablation region of the implant devices by external energy-providing means, which are spatially separated from the implant device, is performed repeatedly at well-spaced time-intervals.
15. A self-expanding implant device adapted to be implanted and deployed within a vessel, said implant comprising an ablation region along at least a portion of its length, the ablation region being adapted for surface contact with the vessel and for subtending at least a substantially complete circumferential band or a spiraling band and said ablation region effective to ablate a signal-blocking path within the vessel upon application of energy to the implant device.
16. An implant according to point 15, whereby said ablation region comprises at least one material which shows magnetic hysteresis, such as a ferromagnetic, ferrimagnetic or anti-ferromagnetic material.
17. An implant according to point 16, whereby said implant devices comprise a ferrous fluid.
18. An implant according to any of the points 15 to 17, comprising a thermoactive coating comprising an activation temperature between 35° C. and 37° C. so that the body temperature would trigger activation.

19. An implant according to any of the points 15 to 17, comprising a thermoactive coating comprising an activation temperature above 45° C. so that activation is triggered only when said ablation region is heated by said external energy-providing means.
20. An implant according to any of the points 15 to 19, comprising substances capable of producing a lesion of limited necrosis and/or neurotoxicity.
21. An implant according to point 20, comprising cavities which are filled with said substances and which open when the implant is heated.
22. An implant according to any of the points 20 or 21, whereby said substances are mixed before being released, e.g. to deliver a two-component neurotoxine.
23. An implant according to any of the points 20 to 22, whereby said substances are a selection or a composition of one or more of the following substances:
    ethanol;
    tetrodotoxin and batrachotoxin;
    maurotoxin, agitoxin, charybdotoxin, margatoxin, slotoxin, scyllatoxin or hefutoxin;
    calciseptine, taicatoxin, calcicludine, or PhTx3;
    botulinum toxide;
    cytochalasin D, rapamycin, sirolimus, zotarolimus, everolimus, paclitaxel;
    glutamate;
    isoquinoline;
    N-methyl-(R)-salsolinol;
    Beta-carboline derivates.
24. An implant according to any of the points 15 to 23, comprising a shape which is adapted for a renal artery.
25. An implant according to point 24, whereby said ablation region of said implant device is adapted for surface contact with said renal arteries and for subtending at least a substantially spiraling band.
26. An implant according to any of the points 15 to 25, comprising a maximal circumference and a minimal circumference and a ratio between maximal and minimal circumference, whereby said ratio is smaller than 7 and larger than 3.
27. An implant according to any of the points 15 to 26, comprising a variable circumference along a longitudinal direction of the implant, said circumference varying between at least 36 mm and at most 250 mm.
28. An implant according to any of the points 15 to 25, comprising an essentially cylindrical shape comprising a diameter which is at least 5 mm and at most 10 mm.
29. An implant according to any of the points 15 to 28, comprising a distal portion and a proximal portion, whereby said ablation region is located within 50% of the implant's total length from the proximal portion.
30. An implant according to any of the points 15 to 29, comprising a distal portion and a proximal portion, whereby said ablation region is located within 15 mm from the proximal portion.
31. An implant according to any of the points 15 to 30, comprising a distal portion and a proximal portion, and comprising an anchoring device connected to the ablation region of said implant via a thermally insulating connection for preventing overheating of said anchoring device, whereby said anchoring device is connected to the distal portion.
32. A system comprising one, two, three, four or more implant devices according to any of the points 15 to 31.
33. A system according to point 32, comprising external energy-providing means, which are spatially separated from said implant devices and able to provide energy to said implant devices for increasing the temperature of the ablation regions of the implant devices up to an ablation temperature.
34. A system according to any of the points 32 or 33, comprising
    a sheath suitable for transporting and delivering the one or more implant devices to or near the desired position in the one or more vessels; and
    a guidewire suitable for sequentially guiding the sheath with the one or more implants to the desired position in the one or more vessels.
35. A system according to any of the points 32 to 34, comprising one or two implant devices according to any of the points 15 to 34, each of which adapted for a corresponding renal artery.

What is claimed is:
1. An implant for treating arterial hypertension by blocking renal sympathetic nerve signals via ablation by heating, comprising an electrical circuit comprising a pickup coil, a heater coil and a temperature-controlled switch which comprises a closed position and an interrupted position, said pick-up coil arranged for inducing an electrical current through at least part of said electrical circuit to which it is connected under the influence of a time-varying magnetic flux through said pickup coil,
    wherein said heating coil is arranged for subtending a substantially spiraling ablation region in a renal artery vessel, for obtaining a substantially spiraling signal-blocking lesion on an inner wall of said renal artery vessel, and wherein said temperature-controlled switch is arranged to change from said closed to said interrupted position when a temperature at or near said implant is higher than a pre-defined ablation temperature.
2. The implant according to claim 1, wherein said implant is at least partly self-expanding.
3. The implant according to claim 1, comprising a cylindrical shape for implantation into a renal artery.
4. The implant according to claim 1, wherein said pickup coil comprises a length which is larger than 15 mm and smaller than 75 mm.
5. The implant according to claim 1, wherein said pickup coil comprises a maximal diameter which is larger than 10 mm and smaller than 60 mm when said implant is in an expanded position.
6. The implant according to claim 1, wherein said heater coil comprises a length which is larger than 3 mm and smaller than 25 mm.
7. The implant according to claim 1, wherein said heater coil comprises a maximal diameter which is larger than 10 mm and smaller than 70 mm when said implant is in an expanded position.
8. The implant according to claim 1, comprising a distance between said pickup coil and said heater coil, said distance being larger than 5 mm and smaller than 50 mm.
9. A system for treating arterial hypertension by blocking renal sympathetic nerve signals via ablation by heating, comprising:
    one or more implants according to claim 1;
    a magnetic field generator for generating a time-varying magnetic field at the position of the one or more implants.
10. The system according to claim 9 wherein said magnetic field generator comprises orientation means for changing the orientation of the time-varying magnetic field generated by said magnetic field generator.

11. The system according to claim 9, wherein the one or more implants comprise two implants.

12. An implant for treating arterial hypertension by blocking renal sympathetic nerve signals via ablation by heating, comprising an electrical circuit comprising a pickup coil, a heater coil and a temperature-dependent LC-circuit, wherein said LC-circuit comprises a resonant frequency which is temperature-dependent.

13. The implant according to claim 12, comprising a cylindrical shape for implantation into a renal artery.

14. A system for treating arterial hypertension by blocking renal sympathetic nerve signals via ablation by heating, comprising:
 an implant according to claim 12;
 a magnetic field generator for generating a time-varying magnetic field at the position of the implant;
 a temperature measurement apparatus arranged for measuring an implant temperature, said measuring of the implant temperature comprising measuring said resonant frequency of said LC-circuit and arranged for relating a measured resonant frequency to the implant temperature;
 temperature controlling means arranged for:
  receiving said implant temperature from said temperature measurement apparatus;
  comparing said implant temperature to a pre-determined ablation temperature;
  controlling the time-varying magnetic field generated by said magnetic field generator on the basis of said comparison.

15. The system according to claim 14, wherein the one or more implants comprise two implants.

16. A method for treating arterial hypertension by blocking renal sympathetic nerve signals via ablation by heating, comprising the steps of:
 implanting one or more implants according to claim 1 in one or more renal arteries;
 applying a time-varying magnetic field at the position of said one or more implants, thereby heating up said one or more implants to a pre-determined ablation temperature.

17. A method for treating arterial hypertension by blocking renal sympathetic nerve signals via ablation by heating, comprising the steps of:
 implanting one or more implants according to claim 12 in one or more renal arteries; applying a time-varying magnetic field at the position of said one or more implants, thereby heating up said one or more implants to a pre-determined ablation temperature.

* * * * *